(12) United States Patent
Metchik et al.

(10) Patent No.: US 11,051,940 B2
(45) Date of Patent: Jul. 6, 2021

(54) PROSTHETIC SPACER DEVICE FOR HEART VALVE

(71) Applicant: Edwards Lifesciences Corporation, Irvine, CA (US)

(72) Inventors: Asher L. Metchik, Hawthorne, CA (US); Sirous Darabian, Lake Forest, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 146 days.

(21) Appl. No.: 16/123,105

(22) Filed: Sep. 6, 2018

(65) Prior Publication Data
US 2019/0069991 A1 Mar. 7, 2019

Related U.S. Application Data
(60) Provisional application No. 62/555,240, filed on Sep. 7, 2017.

(51) Int. Cl.
*A61F 2/24* (2006.01)
*A61B 17/122* (2006.01)
(Continued)

(52) U.S. Cl.
CPC ............ *A61F 2/246* (2013.01); *A61F 2/2466* (2013.01); *A61B 17/1227* (2013.01);
(Continued)

(58) Field of Classification Search
CPC ...... A61F 2/246; A61F 2/2454; A61F 2/2445; A61F 2/2418; A61F 2220/0016;
(Continued)

(56) References Cited

U.S. PATENT DOCUMENTS

| 3,874,368 A | 4/1975 | King et al. |
| 4,340,091 A | 7/1982 | Skelton et al. |

(Continued)

FOREIGN PATENT DOCUMENTS

| CN | 1142351 A | 2/1997 |
| EP | 0098100 A2 | 1/1984 |

(Continued)

OTHER PUBLICATIONS

Rekha Mankad, M.D, "Ejection fraction: What does it measure?", 2019, https://www.mayoclinic.org/ejection-fraction/expert-answers/faq-20058286 (Year: 2019).*

(Continued)

*Primary Examiner* — Majid Jamialahmadi
(74) *Attorney, Agent, or Firm* — Thomas C. Richardson

(57) ABSTRACT

An implantable prosthetic device includes a spacer member configured to be disposed between leaflets of a native heart valve that is located between a first chamber and a second chamber of the heart. The prosthetic device further includes a plurality of anchor members coupled to the spacer member and configured to capture the leaflets between respective anchor members and the spacer member such that the prosthetic device is retained between the leaflets. The spacer member is configured to provide a flow path through the prosthetic device between the first chamber and the second chamber when the leaflets are captured between the anchor members and the spacer member such that blood can flow regurgitatively from the second chamber to the first chamber through the spacer member.

11 Claims, 19 Drawing Sheets

(51) Int. Cl.
  *A61B 17/128* (2006.01)
  *A61F 2/00* (2006.01)
(52) U.S. Cl.
  CPC ... *A61B 17/1285* (2013.01); *A61F 2002/0081* (2013.01); *A61F 2220/0016* (2013.01); *A61F 2230/0093* (2013.01); *A61F 2250/001* (2013.01)
(58) Field of Classification Search
  CPC ............ A61F 2220/0008; A61F 2/2427; A61F 2/2442; A61F 2/2463
  See application file for complete search history.

(56) References Cited

U.S. PATENT DOCUMENTS

| | | |
|---|---|---|
| 4,506,669 A | 3/1985 | Blake, III |
| 4,590,937 A | 5/1986 | Deniega |
| 4,693,248 A | 9/1987 | Failla |
| 4,803,983 A | 2/1989 | Siegel |
| 5,125,895 A | 6/1992 | Buchbinder et al. |
| 5,171,252 A | 12/1992 | Friedland |
| 5,195,962 A | 3/1993 | Martin et al. |
| 5,292,326 A | 3/1994 | Green et al. |
| 5,327,905 A | 7/1994 | Avitall |
| 5,363,861 A | 11/1994 | Edwards et al. |
| 5,370,685 A | 12/1994 | Stevens |
| 5,389,077 A | 2/1995 | Melinyshyn et al. |
| 5,411,552 A | 5/1995 | Andersen et al. |
| 5,450,860 A | 9/1995 | O'Connor |
| 5,456,674 A | 10/1995 | Bos et al. |
| 5,474,057 A | 12/1995 | Makower et al. |
| 5,478,353 A | 12/1995 | Yoon |
| 5,487,746 A | 1/1996 | Yu et al. |
| 5,565,004 A | 10/1996 | Christoudias |
| 5,607,462 A | 3/1997 | Imran |
| 5,609,598 A | 3/1997 | Laufer et al. |
| 5,611,794 A | 3/1997 | Sauer et al. |
| 5,626,607 A | 5/1997 | Malecki et al. |
| 5,695,504 A | 12/1997 | Gifford, III et al. |
| 5,716,417 A | 2/1998 | Girard et al. |
| 5,727,569 A | 3/1998 | Benetti et al. |
| 5,741,297 A | 4/1998 | Simon |
| 5,782,746 A | 7/1998 | Wright |
| 5,797,960 A | 8/1998 | Stevens et al. |
| 5,836,311 A | 11/1998 | Borst et al. |
| 5,843,076 A | 12/1998 | Webster, Jr. et al. |
| 5,855,590 A | 1/1999 | Malecki et al. |
| 5,885,271 A | 3/1999 | Hamilton et al. |
| 5,888,247 A | 3/1999 | Benetti |
| 5,891,017 A | 4/1999 | Swindle et al. |
| 5,891,112 A | 4/1999 | Samson |
| 5,894,843 A | 4/1999 | Benetti et al. |
| 5,921,979 A | 7/1999 | Kovac et al. |
| 5,944,738 A | 8/1999 | Amplatz et al. |
| 5,957,835 A | 9/1999 | Anderson et al. |
| 5,972,020 A | 10/1999 | Carpentier et al. |
| 5,980,534 A | 11/1999 | Gimpelson |
| 6,004,329 A | 12/1999 | Myers et al. |
| 6,010,531 A | 1/2000 | Donlon et al. |
| 6,017,358 A | 1/2000 | Yoon et al. |
| 6,086,600 A | 7/2000 | Kortenbach |
| 6,120,496 A | 9/2000 | Whayne et al. |
| 6,132,370 A | 10/2000 | Furnish et al. |
| 6,162,239 A | 12/2000 | Manhes |
| 6,165,183 A | 12/2000 | Kuehn et al. |
| 6,182,664 B1 | 2/2001 | Cosgrove |
| 6,193,732 B1 | 2/2001 | Frantzen et al. |
| 6,193,734 B1 | 2/2001 | Bolduc et al. |
| 6,200,315 B1 | 3/2001 | Gaiser et al. |
| 6,228,032 B1 | 5/2001 | Eaton et al. |
| 6,241,743 B1 | 6/2001 | Levin et al. |
| 6,269,819 B1 | 8/2001 | Oz et al. |
| 6,269,829 B1 | 8/2001 | Chen et al. |
| 6,312,447 B1 | 11/2001 | Grimes |
| 6,461,366 B1 | 10/2002 | Seguin |
| 6,468,285 B1 | 10/2002 | Hsu et al. |
| 6,508,806 B1 | 1/2003 | Hoste |
| 6,508,825 B1 | 1/2003 | Selmon et al. |
| 6,530,933 B1 | 3/2003 | Yeung et al. |
| 6,537,290 B2 | 3/2003 | Adams et al. |
| 6,544,215 B1 | 4/2003 | Bencini et al. |
| 6,626,930 B1 | 9/2003 | Allen et al. |
| 6,629,534 B1 | 10/2003 | St. Goar et al. |
| 6,695,866 B1 | 2/2004 | Kuehn et al. |
| 6,719,767 B1 | 4/2004 | Kimblad |
| 6,752,813 B2 | 6/2004 | Goldfarb et al. |
| 6,764,510 B2 | 7/2004 | Vidlund et al. |
| 6,770,083 B2 | 8/2004 | Seguin |
| 6,837,867 B2 | 1/2005 | Kortelling |
| 6,855,137 B2 | 2/2005 | Bon |
| 6,875,224 B2 | 4/2005 | Grimes |
| 6,913,614 B2 | 7/2005 | Marino et al. |
| 6,939,337 B2 | 9/2005 | Parker et al. |
| 6,945,956 B2 | 9/2005 | Waldhauser et al. |
| 7,011,669 B2 | 3/2006 | Kimblad |
| 7,048,754 B2 | 5/2006 | Martin et al. |
| 7,101,395 B2 | 9/2006 | Tremulis et al. |
| 7,112,207 B2 | 9/2006 | Allen et al. |
| 7,125,421 B2 | 10/2006 | Tremulis et al. |
| 7,226,467 B2 | 6/2007 | Lucatero et al. |
| 7,288,097 B2 | 10/2007 | Seguin |
| 7,371,210 B2 | 5/2008 | Brock et al. |
| 7,464,712 B2 | 12/2008 | Oz et al. |
| 7,509,959 B2 | 3/2009 | Oz et al. |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,604,646 B2 | 10/2009 | Goldfarb et al. |
| 7,608,091 B2 | 10/2009 | Goldfarb et al. |
| 7,635,329 B2 | 12/2009 | Goldfarb et al. |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,704,269 B2 | 4/2010 | St. Goar et al. |
| 7,731,706 B2 | 6/2010 | Potter |
| 7,736,388 B2 | 6/2010 | Goldfarb et al. |
| 7,744,609 B2 | 6/2010 | Allen et al. |
| 7,748,389 B2 | 7/2010 | Salahieh et al. |
| 7,753,923 B2 | 7/2010 | St. Goar et al. |
| 7,753,932 B2 | 7/2010 | Gingrich et al. |
| 7,758,596 B2 | 7/2010 | Oz et al. |
| 7,780,723 B2 | 8/2010 | Taylor |
| 7,803,185 B2 | 9/2010 | Gabbay |
| 7,811,296 B2 | 10/2010 | Goldfarb et al. |
| 7,824,443 B2 | 11/2010 | Salahieh et al. |
| 7,981,123 B2 | 7/2011 | Seguin |
| 7,988,724 B2 | 8/2011 | Salahieh et al. |
| 7,998,151 B2 | 8/2011 | St. Goar et al. |
| 8,029,518 B2 | 10/2011 | Goldfarb et al. |
| 8,052,592 B2 | 11/2011 | Goldfarb et al. |
| 8,052,749 B2 | 11/2011 | Salahieh et al. |
| 8,052,750 B2 | 11/2011 | Tuval et al. |
| 8,057,493 B2 | 11/2011 | Goldfarb et al. |
| 8,070,805 B2 | 12/2011 | Vidlund et al. |
| 8,096,985 B2 | 1/2012 | Legaspi et al. |
| 8,104,149 B1 | 1/2012 | McGarity |
| 8,123,703 B2 | 2/2012 | Martin et al. |
| 8,133,239 B2 | 3/2012 | Oz et al. |
| 8,147,542 B2 | 4/2012 | Maisano et al. |
| 8,172,856 B2 | 5/2012 | Eigler et al. |
| 8,187,299 B2 | 5/2012 | Goldfarb et al. |
| 8,206,437 B2 | 6/2012 | Bonhoeffer et al. |
| 8,216,256 B2 | 7/2012 | Raschdorf, Jr. et al. |
| 8,216,301 B2 | 7/2012 | Bonhoeffer et al. |
| 8,303,608 B2 | 11/2012 | Goldfarb et al. |
| 8,303,653 B2 | 11/2012 | Bonhoeffer et al. |
| 8,313,525 B2 | 11/2012 | Tuval et al. |
| 8,323,334 B2 | 12/2012 | Deem et al. |
| 8,343,174 B2 | 1/2013 | Goldfarb et al. |
| 8,348,995 B2 | 1/2013 | Tuval et al. |
| 8,348,996 B2 | 1/2013 | Tuval et al. |
| 8,409,273 B2 | 4/2013 | Thornton et al. |

(56) References Cited

U.S. PATENT DOCUMENTS

| | | |
|---|---|---|
| 8,414,643 B2 | 4/2013 | Tuval et al. |
| 8,425,404 B2 | 4/2013 | Wilson et al. |
| 8,449,599 B2 | 5/2013 | Chau et al. |
| 8,449,606 B2 | 5/2013 | Eliasen et al. |
| 8,460,368 B2 | 6/2013 | Taylor et al. |
| 8,470,028 B2 | 6/2013 | Thornton et al. |
| 8,480,730 B2 | 7/2013 | Maurer et al. |
| 8,500,761 B2 | 8/2013 | Goldfarb et al. |
| 8,540,767 B2 | 9/2013 | Zhang |
| 8,579,965 B2 | 11/2013 | Bonhoeffer et al. |
| 8,585,756 B2 | 11/2013 | Bonhoeffer et al. |
| 8,652,202 B2 | 2/2014 | Alon et al. |
| 8,668,733 B2 | 3/2014 | Haug et al. |
| 8,721,665 B2 | 5/2014 | Oz et al. |
| 8,734,505 B2 | 5/2014 | Goldfarb et al. |
| 8,740,918 B2 | 6/2014 | Seguin |
| 8,740,920 B2 | 6/2014 | Goldfarb et al. |
| 8,747,460 B2 | 6/2014 | Tuval et al. |
| 8,771,345 B2 | 7/2014 | Tuval et al. |
| 8,771,346 B2 | 7/2014 | Tuval et al. |
| 8,771,347 B2 | 7/2014 | DeBoer et al. |
| 8,778,017 B2 | 7/2014 | Eliasen et al. |
| 8,834,564 B2 | 9/2014 | Tuval et al. |
| 8,840,663 B2 | 9/2014 | Salahieh et al. |
| 8,676,895 B1 | 11/2014 | Tuval et al. |
| 8,876,894 B2 | 11/2014 | Tuval et al. |
| 8,876,895 B2 | 11/2014 | Tuval et al. |
| 8,926,691 B2 | 1/2015 | Chau et al. |
| 8,945,177 B2 | 2/2015 | Dell et al. |
| 9,011,468 B2 | 4/2015 | Ketai et al. |
| 9,034,032 B2 | 5/2015 | McLean et al. |
| 9,044,246 B2 | 6/2015 | Goldfarb et al. |
| 9,138,312 B2 | 9/2015 | Tuval et al. |
| 9,198,757 B2 | 12/2015 | Schroeder et al. |
| 9,220,507 B1 | 12/2015 | Patel et al. |
| 9,259,317 B2 | 2/2016 | Wilson et al. |
| 9,282,972 B1 | 3/2016 | Patel et al. |
| 9,301,834 B2 | 4/2016 | Tuval et al. |
| 9,308,360 B2 | 4/2016 | Bishop et al. |
| 9,387,071 B2 | 7/2016 | Tuval et al. |
| 9,414,918 B2 | 8/2016 | Chau et al. |
| 9,427,237 B2 | 8/2016 | Oz et al. |
| 9,427,327 B2 | 8/2016 | Parrish |
| 9,439,763 B2 | 9/2016 | Geist et al. |
| 9,510,829 B2 | 12/2016 | Goldfarb et al. |
| 9,510,837 B2 | 12/2016 | Seguin |
| 9,510,946 B2 | 12/2016 | Chau et al. |
| 9,572,660 B2 | 2/2017 | Braido et al. |
| 9,642,704 B2 | 5/2017 | Tuval et al. |
| 9,700,445 B2 | 7/2017 | Martin et al. |
| 9,775,963 B2 | 10/2017 | Miller |
| D809,139 S | 1/2018 | Marsot et al. |
| 9,889,002 B2 | 2/2018 | Bonhoeffer et al. |
| 9,949,824 B2 | 4/2018 | Bonhoeffer et al. |
| 10,076,327 B2 | 9/2018 | Ellis et al. |
| 10,076,415 B1 | 9/2018 | Metchik et al. |
| 10,105,221 B2 | 10/2018 | Siegel |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,226,309 B2 | 3/2019 | Ho et al. |
| 10,231,837 B1 | 3/2019 | Metchik et al. |
| 10,238,493 B1 | 3/2019 | Metchik et al. |
| 10,238,494 B2 | 3/2019 | McNiven et al. |
| 10,238,495 B2 | 3/2019 | Marsot et al. |
| 10,299,924 B2 | 5/2019 | Kizuka |
| 10,376,673 B2 | 8/2019 | Van Hoven et al. |
| 2001/0005787 A1 | 6/2001 | Oz et al. |
| 2002/0013571 A1 | 1/2002 | Goldfarb et al. |
| 2002/0107531 A1 | 8/2002 | Schreck et al. |
| 2002/0173811 A1 | 11/2002 | Tu et al. |
| 2002/0183787 A1 | 12/2002 | Wahr et al. |
| 2003/0144573 A1 | 7/2003 | Heilman et al. |
| 2003/0187467 A1 | 10/2003 | Schreck |
| 2003/0208231 A1 | 11/2003 | Williamson et al. |
| 2004/0003819 A1 | 1/2004 | St. Goar et al. |
| 2004/0034365 A1 | 2/2004 | Lentz et al. |
| 2004/0039442 A1 | 2/2004 | St. Goar et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0127981 A1 | 7/2004 | Randert et al. |
| 2004/0127982 A1 | 7/2004 | Machold et al. |
| 2004/0147943 A1 | 7/2004 | Kobayashi |
| 2004/0167539 A1 | 8/2004 | Kuehn et al. |
| 2004/0181206 A1 | 9/2004 | Chiu et al. |
| 2004/0181238 A1 | 9/2004 | Zarbatany et al. |
| 2004/0210307 A1 | 10/2004 | Khairkhahan |
| 2004/0220593 A1 | 11/2004 | Greenhalgh |
| 2005/0010287 A1 | 1/2005 | Macoviak et al. |
| 2005/0033446 A1 | 2/2005 | Deem et al. |
| 2005/0049618 A1 | 3/2005 | Masuda et al. |
| 2005/0137690 A1 | 6/2005 | Salahieh et al. |
| 2005/0143767 A1 | 6/2005 | Kimura et al. |
| 2005/0165429 A1 | 7/2005 | Douglas et al. |
| 2005/0216039 A1 | 9/2005 | Lederman |
| 2005/0251183 A1 | 11/2005 | Buckman et al. |
| 2005/0288786 A1 | 12/2005 | Chanduszko |
| 2006/0020275 A1 | 1/2006 | Goldfarb et al. |
| 2006/0089671 A1 | 4/2006 | Goldfarb et al. |
| 2006/0100649 A1 | 5/2006 | Hart |
| 2006/0122647 A1 | 6/2006 | Callaghan et al. |
| 2006/0142694 A1 | 6/2006 | Bednarek et al. |
| 2006/0178700 A1 | 8/2006 | Quinn |
| 2006/0224169 A1 | 10/2006 | Weisenburgh et al. |
| 2007/0010800 A1 | 1/2007 | Weitzner et al. |
| 2007/0010877 A1 | 1/2007 | Salahieh et al. |
| 2007/0016286 A1 | 1/2007 | Herrmann et al. |
| 2007/0021779 A1 | 1/2007 | Garvin et al. |
| 2007/0032807 A1 | 2/2007 | Ortiz et al. |
| 2007/0038293 A1 | 2/2007 | St. Goar et al. |
| 2007/0093857 A1 | 4/2007 | Rogers et al. |
| 2007/0093890 A1 | 4/2007 | Eliasen et al. |
| 2007/0100356 A1 | 5/2007 | Lucatero et al. |
| 2007/0129737 A1 | 6/2007 | Goldfarb et al. |
| 2007/0156197 A1 | 7/2007 | Root et al. |
| 2007/0191154 A1 | 8/2007 | Genereux et al. |
| 2007/0197858 A1 | 8/2007 | Goldfarb et al. |
| 2007/0198038 A1 | 8/2007 | Cohen et al. |
| 2007/0265700 A1 | 11/2007 | Eliasen et al. |
| 2007/0282414 A1 | 12/2007 | Soltis et al. |
| 2007/0293943 A1 | 12/2007 | Quinn |
| 2007/0299387 A1 | 12/2007 | Williams et al. |
| 2007/0299424 A1 | 12/2007 | Cumming et al. |
| 2008/0039743 A1 | 2/2008 | Fox et al. |
| 2008/0039953 A1 | 2/2008 | Davis et al. |
| 2008/0065149 A1 | 3/2008 | Thielen et al. |
| 2008/0077144 A1 | 3/2008 | Crofford |
| 2008/0091169 A1 | 4/2008 | Heideman et al. |
| 2008/0140089 A1 | 6/2008 | Kogiso et al. |
| 2008/0147093 A1 | 6/2008 | Roskopf et al. |
| 2008/0147112 A1 | 6/2008 | Sheets et al. |
| 2008/0167713 A1 | 7/2008 | Bolling |
| 2008/0167714 A1 | 7/2008 | St. Goar et al. |
| 2008/0177300 A1 | 7/2008 | Mas et al. |
| 2008/0208332 A1 | 8/2008 | Lamphere et al. |
| 2008/0221672 A1 | 9/2008 | Lamphere et al. |
| 2008/0255427 A1 | 10/2008 | Satake et al. |
| 2008/0281411 A1 | 11/2008 | Berreklouw |
| 2008/0287862 A1 | 11/2008 | Weitzner et al. |
| 2008/0294247 A1 | 11/2008 | Yang et al. |
| 2008/0312506 A1 | 12/2008 | Spivey et al. |
| 2008/0319455 A1 | 12/2008 | Harris et al. |
| 2009/0005863 A1 | 1/2009 | Goetz et al. |
| 2009/0024110 A1 | 1/2009 | Heideman et al. |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. et al. |
| 2009/0166913 A1 | 7/2009 | Guo et al. |
| 2009/0177266 A1 | 7/2009 | Powell et al. |
| 2009/0275902 A1 | 11/2009 | Heeps et al. |

(56) References Cited

U.S. PATENT DOCUMENTS

| | | |
|---|---|---|
| 2009/0287304 A1 | 11/2009 | Dahlgren et al. |
| 2010/0022823 A1 | 1/2010 | Goldfarb et al. |
| 2010/0057192 A1 | 3/2010 | Celermajer |
| 2010/0094317 A1 | 4/2010 | Goldfarb et al. |
| 2010/0106141 A1 | 4/2010 | Osypka et al. |
| 2010/0121434 A1 | 5/2010 | Paul et al. |
| 2010/0217283 A1 | 8/2010 | St. Goar et al. |
| 2010/0249497 A1 | 9/2010 | Peine et al. |
| 2010/0298929 A1 | 11/2010 | Thornton et al. |
| 2010/0324595 A1 | 12/2010 | Linder et al. |
| 2011/0082538 A1 | 4/2011 | Dahlgren et al. |
| 2011/0137397 A1* | 6/2011 | Chau ............... A61F 2/2418 623/1.11 |
| 2011/0137410 A1 | 6/2011 | Hacohen |
| 2011/0245855 A1 | 10/2011 | Matsuoka et al. |
| 2011/0257723 A1 | 10/2011 | McNamara |
| 2011/0295281 A1 | 12/2011 | Mizumoto et al. |
| 2012/0022633 A1 | 1/2012 | Olson et al. |
| 2012/0046741 A1 | 2/2012 | Tuval et al. |
| 2012/0089125 A1 | 4/2012 | Scheibe et al. |
| 2012/0109160 A1 | 5/2012 | Martinez et al. |
| 2012/0116419 A1 | 5/2012 | Sigmon, Jr. |
| 2012/0209318 A1 | 8/2012 | Qadeer |
| 2012/0277853 A1 | 11/2012 | Rothstein |
| 2013/0035759 A1 | 2/2013 | Gross et al. |
| 2013/0041314 A1 | 2/2013 | Dillon |
| 2013/0066341 A1 | 3/2013 | Ketai et al. |
| 2013/0066342 A1* | 3/2013 | Dell ............... A61F 2/2454 606/151 |
| 2013/0072945 A1 | 3/2013 | Terada |
| 2013/0073034 A1 | 3/2013 | Wilson et al. |
| 2013/0110254 A1 | 5/2013 | Osborne |
| 2013/0190798 A1 | 7/2013 | Kapadia |
| 2013/0190861 A1 | 7/2013 | Chau et al. |
| 2013/0232059 A1 | 10/2013 | Ketai et al. |
| 2013/0268069 A1 | 10/2013 | Zakai et al. |
| 2013/0304197 A1 | 11/2013 | Buchbinder et al. |
| 2013/0325110 A1 | 12/2013 | Khalil et al. |
| 2014/0031928 A1 | 1/2014 | Murphy et al. |
| 2014/0046433 A1 | 2/2014 | Kovalsky |
| 2014/0046434 A1 | 2/2014 | Rolando et al. |
| 2014/0052237 A1 | 2/2014 | Lane et al. |
| 2014/0058411 A1 | 2/2014 | Soutorine et al. |
| 2014/0066693 A1 | 3/2014 | Goldfarb et al. |
| 2014/0067048 A1 | 3/2014 | Chau et al. |
| 2014/0067052 A1 | 3/2014 | Chau et al. |
| 2014/0094903 A1 | 4/2014 | Miller et al. |
| 2014/0135685 A1 | 5/2014 | Kabe et al. |
| 2014/0194975 A1 | 7/2014 | Quill et al. |
| 2014/0200662 A1 | 7/2014 | Eftel et al. |
| 2014/0207231 A1 | 7/2014 | Hacohen et al. |
| 2014/0236198 A1 | 8/2014 | Goldfarb et al. |
| 2014/0243968 A1 | 8/2014 | Padala |
| 2014/0251042 A1 | 9/2014 | Asselin et al. |
| 2014/0277404 A1 | 9/2014 | Wilson et al. |
| 2014/0277411 A1 | 9/2014 | Bortlein et al. |
| 2014/0316428 A1 | 10/2014 | Golan |
| 2014/0324164 A1 | 10/2014 | Gross et al. |
| 2014/0330368 A1 | 11/2014 | Gloss et al. |
| 2014/0336751 A1 | 11/2014 | Kramer |
| 2014/0371843 A1 | 12/2014 | Wilson et al. |
| 2015/0039084 A1 | 2/2015 | Levi et al. |
| 2015/0057704 A1 | 2/2015 | Takahashi |
| 2015/0094802 A1 | 4/2015 | Buchbinder et al. |
| 2015/0100116 A1 | 4/2015 | Mohl et al. |
| 2015/0105808 A1 | 4/2015 | Gordon et al. |
| 2015/0148896 A1 | 5/2015 | Karapetian et al. |
| 2015/0157268 A1 | 6/2015 | Winshtein |
| 2015/0182223 A1 | 7/2015 | Ketai et al. |
| 2015/0196390 A1 | 7/2015 | Ma et al. |
| 2015/0223793 A1 | 8/2015 | Goldfarb et al. |
| 2015/0230919 A1 | 8/2015 | Chau et al. |
| 2015/0238313 A1 | 8/2015 | Spence et al. |
| 2015/0257757 A1 | 9/2015 | Powers et al. |
| 2015/0257877 A1 | 9/2015 | Hernandez |
| 2015/0257883 A1 | 9/2015 | Basude et al. |
| 2015/0313592 A1 | 11/2015 | Coillard-Lavirotte et al. |
| 2015/0351904 A1 | 12/2015 | Cooper et al. |
| 2015/0366666 A1 | 12/2015 | Khairkhahan et al. |
| 2016/0008131 A1 | 1/2016 | Christianson et al. |
| 2016/0022970 A1 | 1/2016 | Forcucci et al. |
| 2016/0106539 A1 | 4/2016 | Buchbinder et al. |
| 2016/0113762 A1 | 4/2016 | Clague et al. |
| 2016/0113764 A1 | 4/2016 | Sheahan et al. |
| 2016/0113766 A1 | 4/2016 | Ganesan et al. |
| 2016/0155987 A1 | 6/2016 | Yoo et al. |
| 2016/0174979 A1 | 6/2016 | Wei |
| 2016/0174981 A1 | 6/2016 | Fago et al. |
| 2016/0242906 A1 | 8/2016 | Morriss et al. |
| 2016/0287387 A1 | 10/2016 | Wei |
| 2016/0317290 A1 | 11/2016 | Chau et al. |
| 2016/0324634 A1 | 11/2016 | Gabbay |
| 2016/0331523 A1 | 11/2016 | Chau et al. |
| 2016/0354082 A1 | 12/2016 | Oz et al. |
| 2017/0020521 A1 | 1/2017 | Krone et al. |
| 2017/0035561 A1 | 2/2017 | Rowe et al. |
| 2017/0035566 A1 | 2/2017 | Krone et al. |
| 2017/0042456 A1 | 2/2017 | Budiman |
| 2017/0042678 A1 | 2/2017 | Ganesan et al. |
| 2017/0049455 A1 | 2/2017 | Seguin |
| 2017/0100236 A1 | 4/2017 | Robertson et al. |
| 2017/0239048 A1 | 8/2017 | Goldfarb et al. |
| 2017/0252154 A1 | 9/2017 | Tubishevitz et al. |
| 2017/0281330 A1 | 10/2017 | Liljegren et al. |
| 2017/0348102 A1 | 12/2017 | Cousins et al. |
| 2018/0000582 A1 | 1/2018 | Tuval et al. |
| 2018/0008311 A1 | 1/2018 | Shiroff et al. |
| 2018/0021044 A1 | 1/2018 | Miller et al. |
| 2018/0021129 A1 | 1/2018 | Peterson et al. |
| 2018/0021134 A1 | 1/2018 | McNiven et al. |
| 2018/0078271 A1 | 3/2018 | Thrasher, III |
| 2018/0126124 A1 | 5/2018 | Winston et al. |
| 2018/0146964 A1 | 5/2018 | Garcia et al. |
| 2018/0146966 A1 | 5/2018 | Hernandez et al. |
| 2018/0153552 A1 | 6/2018 | King et al. |
| 2018/0161159 A1 | 6/2018 | Lee et al. |
| 2018/0168803 A1 | 6/2018 | Pesce et al. |
| 2018/0221147 A1 | 8/2018 | Ganesan et al. |
| 2018/0235657 A1 | 8/2018 | Abunassar |
| 2018/0243086 A1 | 8/2018 | Barbarino et al. |
| 2018/0258665 A1 | 9/2018 | Reddy et al. |
| 2018/0263767 A1 | 9/2018 | Chau et al. |
| 2018/0296326 A1 | 10/2018 | Dixon et al. |
| 2018/0296327 A1 | 10/2018 | Dixon et al. |
| 2018/0296328 A1 | 10/2018 | Dixon et al. |
| 2018/0296329 A1 | 10/2018 | Dixon et al. |
| 2018/0296330 A1 | 10/2018 | Dixon et al. |
| 2018/0296331 A1 | 10/2018 | Dixon et al. |
| 2018/0296332 A1 | 10/2018 | Dixon et al. |
| 2018/0296333 A1 | 10/2018 | Dixon et al. |
| 2018/0296334 A1 | 10/2018 | Dixon et al. |
| 2018/0325661 A1 | 11/2018 | Delgado et al. |
| 2018/0325671 A1 | 11/2018 | Abunassar et al. |
| 2018/0333259 A1 | 11/2018 | Dibie |
| 2018/0344457 A1 | 12/2018 | Gross et al. |
| 2018/0353181 A1 | 12/2018 | Wei |
| 2019/0000613 A1 | 1/2019 | Delgado et al. |
| 2019/0000623 A1 | 1/2019 | Pan et al. |
| 2019/0008642 A1 | 1/2019 | Delgado et al. |
| 2019/0008643 A1 | 1/2019 | Delgado et al. |
| 2019/0015199 A1 | 1/2019 | Delgado et al. |
| 2019/0015200 A1 | 1/2019 | Delgado et al. |
| 2019/0015207 A1 | 1/2019 | Delgado et al. |
| 2019/0015208 A1 | 1/2019 | Delgado et al. |
| 2019/0021652 A1 | 1/2019 | Delgado et al. |
| 2019/0021851 A1 | 1/2019 | Delgado et al. |
| 2019/0029498 A1 | 1/2019 | Mankowski et al. |
| 2019/0029810 A1 | 1/2019 | Delgado et al. |
| 2019/0029813 A1 | 1/2019 | Delgado et al. |
| 2019/0030285 A1 | 1/2019 | Prabhu et al. |
| 2019/0053810 A1 | 2/2019 | Griffin |
| 2019/0060058 A1 | 2/2019 | Delgado et al. |
| 2019/0060059 A1 | 2/2019 | Delgado et al. |
| 2019/0060072 A1 | 2/2019 | Zeng |

(56) References Cited

U.S. PATENT DOCUMENTS

| | | |
|---|---|---|
| 2019/0060073 A1 | 2/2019 | Delgado et al. |
| 2019/0060074 A1 | 2/2019 | Delgado et al. |
| 2019/0060075 A1 | 2/2019 | Delgado et al. |
| 2019/0069991 A1 | 3/2019 | Metchik et al. |
| 2019/0069992 A1 | 3/2019 | Delgado et al. |
| 2019/0069993 A1 | 3/2019 | Delgado et al. |
| 2019/0105156 A1 | 4/2019 | He et al. |
| 2019/0111239 A1 | 4/2019 | Bolduc et al. |
| 2019/0142589 A1 | 5/2019 | Basude |
| 2019/0159782 A1 | 5/2019 | Kamaraj et al. |
| 2019/0167197 A1 | 6/2019 | Abunassar et al. |
| 2019/0209323 A1 | 7/2019 | Metchik et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0314155 A1 | 10/2019 | Franklin et al. |
| 2020/0113683 A1 | 4/2020 | Dale et al. |

FOREIGN PATENT DOCUMENTS

| | | |
|---|---|---|
| EP | 0879069 B1 | 8/2003 |
| EP | 1281375 A3 | 12/2003 |
| EP | 1301235 B1 | 10/2004 |
| EP | 1583577 B1 | 5/2007 |
| EP | 1408850 B1 | 9/2009 |
| EP | 0930845 B1 | 10/2009 |
| EP | 1624810 B1 | 3/2011 |
| EP | 1804686 B1 | 9/2015 |
| EP | 2428169 B1 | 10/2016 |
| EP | 2266503 B1 | 1/2017 |
| EP | 2266504 B1 | 3/2017 |
| FR | 2146050 A5 | 2/1973 |
| FR | 9711600 | 3/1997 |
| FR | 2 768 324 A1 | 3/1999 |
| JP | 2014000417 A | 1/2014 |
| WO | 9802103 A1 | 1/1998 |
| WO | 9900059 A1 | 1/1999 |
| WO | 9913777 A1 | 3/1999 |
| WO | 0060995 A3 | 4/2001 |
| WO | 03001893 A2 | 1/2003 |
| WO | 2004103162 A2 | 12/2004 |
| WO | 2004103434 A2 | 12/2004 |
| WO | 2005112792 A2 | 12/2005 |
| WO | 2006086434 A1 | 8/2006 |
| WO | 2006116558 A2 | 11/2006 |
| WO | 2006138173 A3 | 3/2007 |
| WO | 2006047709 A3 | 7/2007 |
| WO | 2008147964 A1 | 12/2008 |
| WO | 2008150529 A1 | 12/2008 |
| WO | 2009024859 A3 | 5/2009 |
| WO | 2009108942 A1 | 9/2009 |
| WO | 2009053952 A3 | 12/2009 |
| WO | 2009116041 A3 | 3/2010 |
| WO | 2010098804 A1 | 9/2010 |
| WO | 2010128502 A1 | 11/2010 |
| WO | 2011034628 A1 | 3/2011 |
| WO | 2013059747 A1 | 4/2013 |
| WO | 2016110760 A1 | 7/2016 |
| WO | 2017015632 A1 | 1/2017 |
| WO | 2018013856 A1 | 1/2018 |
| WO | 2018050200 A1 | 3/2018 |
| WO | 2018050203 A1 | 3/2018 |
| WO | 2018195015 A1 | 10/2018 |
| WO | 2018195201 A1 | 10/2018 |
| WO | 2018195215 A2 | 10/2018 |
| WO | 2019139904 A1 | 7/2019 |

OTHER PUBLICATIONS

"Echocardiography Calculator"; https://www.zunis.org/Mitral%20Regurgitation.htm; 2002; p. 2 table labled "Mitral Regurgitation".*

Reul RM et al., "Mitral valve reconstruction for mitral insufficiency", Prog Cardiovasc Dis., vol. 39, Issue-6, May-Jun. 1997.

Batista RJ et al., "Partial left ventriculectomy to treat end-stage heart disease", Ann Thorac Surg., vol. 64, Issue-3, pp. 634-638, Sep. 1997.

Beall AC Jr. et al.,"Clinical experience with a dacron velour-covered teflon-disc mitral-valve prosthesis", Ann Thorac Surg., vol.-5, Issue 5, pp. 402-410, May 1968.

Fucci et al., "Improved results with mitral valve repair using new surgical techniques", Eur J Cardiothorac Surg. 1995;Issue 9, vol.-11, pp. 621-626.

Maisano F et al., 'The edge-to-edge technique: a simplified method to correct mitral insufficiency', Eur J Cardiothorac Surg., vol. 13, Issue-3, pp. 240-245, Mar. 1998.

Umaña JP et al., "'Bow-tie' mitral valve repair: an adjuvant technique for ischemic mitral regurgitation', Ann Thorac Surg., vol. 66, Issue-6, pp. 1640-1646, Nov. 1998.

Al-Khaja et al., "Eleven Years' Experience with Carpentier-Edwards Biological Valves in Relation to Survival and Complications", European Journal of Cardio-thoracic Surgery 3: pp. 305-311, 1989.

Almagor et al., "Balloon Expandable Stent Implantation in Stenotic Right Heart Valved Conduits", Journal of the American College of Cardiology, vol. 16, No. 6, pp. 1310-1314, Nov. 15, 1990.

Al Zaibag et al., "Percutaneous Balloon Valvotomy in Tricuspid Stenosis", British Heart Journal, vol. 57, No. 1, Jan. 1987.

Andersen, et al., "Transluminal implantation of artificial heart valves. Description of a new expandable aortic valve and initial results with implantation by catheter technique in closed chest pigs." European Heart Journal (1992), 13, 704-708.

Andersen, H.R. "History of Percutaneous Aortic Valve Prosthesis," Herz No. 34. pp. 343-346. 2009.

Benchimol et al., "Simultaneous Left Ventricular Echocardiography and Aortic Blood Velocity During Rapid Right Ventricular Pacing in Man", The American Journal of the Medical Sciences, vol. 273, No. 1, pp. 55-62, 1977.

Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.

Dotter et al., "Transluminal Treatment of Arteriosclerotic Obstruction: Description of a New Technic and a Preliminary Report of Its Application", Circulation, vol. XXX, pp. 654-670, 1964.

Kolata, Gina "Device that Opens Clogged Arteries Gets a Failing Grade in a New Study", The New York Times, http://www.nytimes.com/1991/01/03/health/device-that-opens-clogged-arteries-gets-a-faili . . ., pp. 1-2, wrriten Jan. 3, 199, web page access Jul. 29, 2009.

Inoune, M.D., Kanji, et al., "Clinical Application of Transvenous Mitral Commissurotomy by a New Balloon Catheter," The Journal of Thoracic and Cardiovascular Surgery 87:394-402, 1984.

Lawrence, Jr., et al., "Percutaneous Endovascular Graft: Experimental Evaluation", Cardiovascular Radiology 163, pp. 357-360, May 1987.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Porstmann et al., "Der Verschluβ des Ductus Arteriosus Persistens Ohne Thorakotomie", Thoraxchirurgie Vaskuläre Chirurgie, Band 15, Heft 2, Stuttgart, im Apr. 1967, pp. 199-203.

Praz et al., "Compassionate use of the PASCAL transcatheter mitral valve repair system for patients with severe mitral regurgitation: a multicentre, prospective, observational, first-in-man study," Lancet vol. 390, pp. 773-780, 2017.

Rashkind et al., "Creation of an Atrial Septal Defect Without Thoracotomy: A Pallative Approach to Complete Transposition of the Great Arteries", The Journal of the American Medical Association, vol. 196, No. 11, pp. 173-174, Jun. 13, 1956.

Rashkind et al., "Historical Aspects of Interventional Cardiology: Past, Present, and Future", Texas Heart Institute Journal, Interventional Cardiology, pp. 363-367.

Rosch, M.D., Josef, "The Birth, Early Years and Future of Interventional Radiology," J Vasc Interv Radiol 2003; 14:841-853.

Ross, D.N, "Aortic Valve Surgery", Surgery of the Aortic Valves, Guy's Hospital, London, pp. 192-197.

(56) References Cited

OTHER PUBLICATIONS

Sabbah et al., "Mechanical Factors in the Degeneration of Porcine Bioprosthetic Valves: An Overview", Journal of Cardiac Surgery, vol. 4, No. 4, pp. 302-309, Dec. 1989.
Selby et al., "Experience with New Retrieval Forceps for Foreign Body Removal in the Vascular, Urinary, and Biliary Systems", Radiology: 176. pp. 535-538, 1990.
Serruys et al., "Stenting of Coronary Arteries. Are we the Sorcerer's Apprentice?", European Heart Journal, 10, 774-782, pp. 37-45, 1989.
Sigwart, Ulrich, "An Overview of Intravascular Stents: Old and New," Chapter 48, Textbook of Interventional Cardiology, 2nd Edition, W.B. Saunders Company, Philadelphia, PA, ©1994, 1990, pp. 803-815.
Uchida et al., "Modifications of Gianturco Expandable Wire Stents", Technical Note, American Roentgen Ray Society, pp. 1185-1187, May 1988.
Urban, Philip MD, "Coronary Artery Stenting", Editions Medecine et Hygiene, Geneve, pp. 1-47, 1991.
Watt et al., "Intravenous Adenosine in the Treatment of Supraventricular Tachycardia: A Dose-Ranging Study and Interaction with Dipyridamole", Br. J. Clin. Pharmac. 21, pp. 227-230, 1986.
Wheatley, David J., "Valve Prosthesis", Rob & Smith's Operative Surgery, pp. 415-424, 1986.

\* cited by examiner

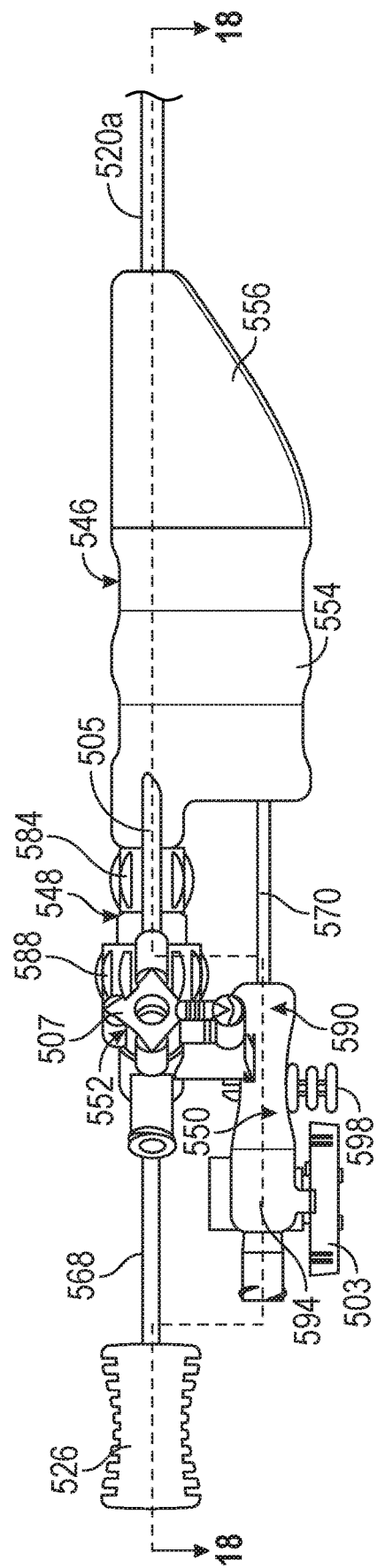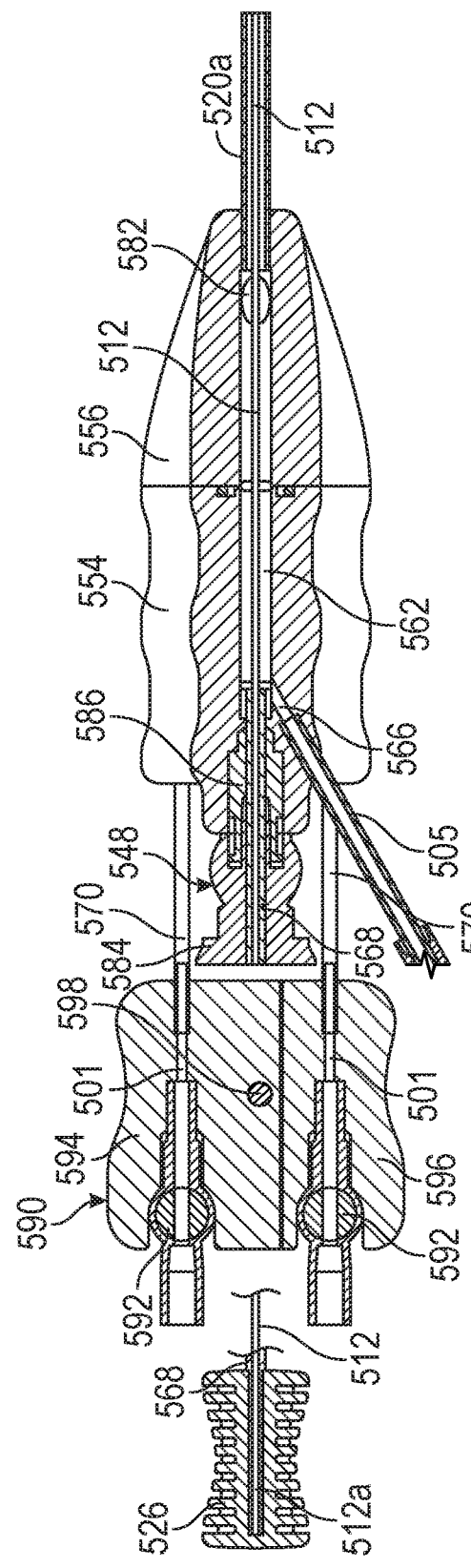
FIG. 17
FIG. 18

PROSTHETIC SPACER DEVICE FOR HEART VALVE

CROSS REFERENCE TO RELATED APPLICATION

This application claims the benefit of U.S. Provisional Application No. 62/555,240, filed on Sep. 7, 2017, which is incorporated herein by reference in its entirety.

FIELD

The present application concerns devices and methods for treating regurgitant heart valves, such as the mitral valve.

BACKGROUND

The native heart valves (e.g., the aortic, pulmonary, tricuspid and mitral valves) serve critical functions in assuring the forward flow of an adequate supply of blood through the cardiovascular system. These heart valves can be damaged, and thus rendered less effective, by congenital malformations, inflammatory processes, infectious conditions, or disease. Such damage to the valves can result in serious cardiovascular compromise or death. For many years the definitive treatment for such damaged valves was surgical repair or replacement of the valve during open heart surgery. However, open heart surgeries are highly invasive and are prone to many complications. Therefore, high-risk patients, including elderly and frail patients with defective heart valves, often went untreated. More recently, transvascular techniques have been developed for introducing and implanting prosthetic devices in a manner that is much less invasive than open heart surgery. One particular transvascular technique that is used for accessing the native mitral and aortic valves is the transseptal technique. The transseptal technique comprises inserting a catheter into the right femoral vein, up the inferior vena cava and into the right atrium. The septum is then punctured and the catheter passed into the left atrium. Such transvascular techniques have increased in popularity due to their high success rates.

A healthy heart has a generally conical shape that tapers to a lower apex. The heart is four-chambered and comprises the left atrium, right atrium, left ventricle, and right ventricle. The left and right sides of the heart are separated by a wall generally referred to as the septum. The native mitral valve of the human heart connects the left atrium to the left ventricle. The mitral valve has a very different anatomy than other native heart valves. The mitral valve includes an annulus portion, which is an annular portion of the native valve tissue surrounding the mitral valve orifice, and a pair of cusps, or leaflets, extending downward from the annulus into the left ventricle. The mitral valve annulus can form a "D"-shaped, oval, or otherwise out-of-round cross-sectional shape having major and minor axes. The anterior leaflet can be larger than the posterior leaflet, forming a generally "C"-shaped boundary between the abutting free edges of the leaflets when they are closed together.

When operating properly, the anterior leaflet and the posterior leaflet function together as a one-way valve to allow blood to flow only from the left atrium to the left ventricle. The left atrium receives oxygenated blood from the pulmonary veins. When the muscles of the left atrium contract and the left ventricle dilates (also referred to as "ventricular diastole" or "diastole"), the oxygenated blood that is collected in the left atrium flows into the left ventricle. When the muscles of the left atrium relax and the muscles of the left ventricle contract (also referred to as "ventricular systole" or "systole"), the increased blood pressure in the left ventricle urges the two leaflets together, thereby closing the one-way mitral valve so that blood cannot flow back to the left atrium and is instead expelled out of the left ventricle through the aortic valve. To prevent the two leaflets from prolapsing under pressure and folding back through the mitral annulus toward the left atrium, a plurality of fibrous cords called chordae tendineae tether the leaflets to papillary muscles in the left ventricle.

Mitral regurgitation occurs when the native mitral valve fails to close properly and blood flows into the left atrium from the left ventricle during the systolic phase of heart contraction. Mitral regurgitation is the most common form of valvular heart disease. Mitral regurgitation has different causes, such as leaflet prolapse, dysfunctional papillary muscles and/or stretching of the mitral valve annulus resulting from dilation of the left ventricle. Mitral regurgitation at a central portion of the leaflets can be referred to as central jet mitral regurgitation and mitral regurgitation nearer to one commissure (i.e., location where the leaflets meet) of the leaflets can be referred to as eccentric jet mitral regurgitation.

Some prior techniques for treating mitral regurgitation include stitching portions of the native mitral valve leaflets directly to one another (known as the "Alfieri stitch"). Other prior techniques include the use of a leaflet clip, such as the Abbot Laboratories MitraClip®, that is clipped onto the coaptation edges of the native mitral valve leaflets and holds them together to mimic an Alfieri stitch. Unfortunately, the MitraClip® device suffers from a number of drawbacks. For example, securing the leaflets directly to each other can place undue stress on the leaflets, which can cause tearing and single leaflet detachment. Also, the MitraClip® device has a relatively narrow profile and can only capture a very small area of the leaflets, which can create areas of stress on the leaflets and possible trauma to the leaflets. Fastening the leaflets directly to each other also prevents the captured portions of the coaptation edges from separating during ventricular diastole, which can inhibit antegrade blood flow through the mitral valve.

Moreover, the procedure for implanting the MitraClip device is relatively difficult and time consuming for a number of reasons. For example, it is difficult to properly position the device so that the clipping members are behind the native leaflets, which are moving during the cardiac cycle. Further, when positioning or retrieving the MitraClip® device the clipping members can become entangled or catch onto adjacent tissue, such as the chordae tendineae. Removing the device from the entangled tissue can be difficult and can cause trauma to the tissue. Another drawback is that a single MitraClip® device typically will not adequately reduce mitral regurgitation because only a very small area of the leaflets are held together. As such, multiple devices, such as two to four devices, typically are required to adequately address the regurgitation, which further adds to the complexity and time required to complete the procedure.

Furthermore, it is difficult to manipulate the distal end portion of the MitraClip® delivery system within the small confines of the left atrium. For example, the MitraClip® delivery system does not permit independent positioning of the implant in the anterior-posterior directions, superior-inferior directions, and the medial-lateral directions. Due to limitations of the MitraClip® delivery system, adjustment of the delivery system in the medial-lateral direction, for example, will change the superior-inferior positioning of the implant. Thus, positioning the implant at the desired location along the coaptation edge using the MitraClip® delivery system is difficult and/or time consuming.

Accordingly, there is a continuing need for improved devices and methods for treating mitral valve regurgitation.

SUMMARY

Certain embodiments of the disclosure concern devices and methods for treating regurgitant heart valves. For example, in a representative embodiment, an implantable prosthetic device comprises a spacer member configured to be disposed between leaflets of a native heart valve that is located between a first chamber and a second chamber of the heart. The prosthetic device further comprises a plurality of anchor members coupled to the spacer member and configured to capture the leaflets between respective anchor members and the spacer member such that the prosthetic device is retained between the leaflets. The spacer member is configured to provide a flow path through the prosthetic device between the first chamber and the second chamber when the leaflets are captured between the anchor members and the spacer member such that blood can flow regurgitatively from the second chamber to the first chamber through the spacer member.

In some embodiments, the spacer member comprises a porous body.

In some embodiments, the porous body comprises a wire mesh.

In some embodiments, the first chamber is a left ventricle and the second chamber is a left atrium, and the spacer member is configured to allow a regurgitant blood flow volume through the device from the left ventricle to the left atrium of from 5% to 30% of a left ventricle stroke volume of the left ventricle at the time the device is implanted.

In some embodiments, the spacer member comprises a porous covering.

In some embodiments, the porous covering comprises a knitted fabric.

In some embodiments, the porous covering comprises an openwork fabric.

In some embodiments, the first chamber is a left ventricle and the second chamber is a left atrium, and the porous covering is configured to promote tissue ingrowth such that regurgitant blood flow through the device from the left ventricle to the left atrium is reduced from 15% to 30% of a left ventricle stroke volume of the left ventricle at the time the device is implanted, to 0% to 20% of a left ventricle stroke volume of the left ventricle over a time period of one month to six months.

In some embodiments, the native heart valve is a mitral valve, and the porous covering is configured to promote tissue ingrowth such that regurgitant blood flow through the device from the second chamber to the first chamber is reduced from a volume equivalent to mitral regurgitation having an angiographic grade of MR≥3+ at the time the device is implanted, to a volume equivalent to mitral regurgitation having an angiographic grade of MR≤2+ over a time period of one month to six months.

In some embodiments, the native heart valve is a mitral valve, the prosthetic device is coupled to a delivery apparatus prior to implantation, and the prosthetic device is configured to allow regurgitant blood flow through the spacer member after the prosthetic device is released from the delivery apparatus. A volume of the regurgitant blood flow is equivalent to mitral regurgitation having an angiographic grade of MR>2+.

In some embodiments, the prosthetic device is configured to allow regurgitant blood flow through the spacer member having a volume equivalent to mitral regurgitation having an angiographic grade of MR>3+.

In some embodiments, the prosthetic device is configured to allow regurgitant blood flow through the spacer member having a volume equivalent to mitral regurgitation having an angiographic grade of MR>4+.

In another representative embodiment, a method of implanting a prosthetic device comprises advancing a prosthetic device in a compressed configuration to a native heart valve using a delivery apparatus. The prosthetic device comprises a spacer member and a plurality of anchor members, and the native heart valve is located between a first chamber and a second chamber of the heart. The method further comprises radially expanding the prosthetic device from the compressed configuration to an expanded configuration, and positioning the prosthetic device such that the spacer member is located between leaflets of the native heart valve. The method further comprises capturing the leaflets between the anchor members and the spacer member such that the prosthetic device is retained between the leaflets, and such that blood flows regurgitatively through the spacer member from the second chamber to the first chamber. The method further comprises releasing the prosthetic device from the delivery apparatus.

In some embodiments, the first chamber is a left atrium, the second chamber is a left ventricle, and the native heart valve is a mitral valve, prior to implanting the prosthetic device, a left ventricle ejection fraction of the left ventricle is less than 20% of an end-diastolic volume of the left ventricle.

In some embodiments, the first chamber is a left atrium, the second chamber is a left ventricle, and the native heart valve is a mitral valve, and after the prosthetic device is released, a volume of the regurgitant blood flow through the spacer member is equivalent to mitral regurgitation having an angiographic grade of MR>2+.

In some embodiments, the volume of the regurgitant blood flow through the spacer member is equivalent to mitral regurgitation having an angiographic grade of MR>3+.

In some embodiments, the first chamber is a left ventricle and the second chamber is a left atrium, and after capturing the leaflets, the spacer member is configured to allow a regurgitant blood flow volume through the device from the left ventricle to the left atrium of from 5% to 30% of a left ventricle stroke volume of the left ventricle.

In some embodiments, the spacer member comprises a wire mesh.

In some embodiments, the spacer member comprises a porous covering.

In some embodiments, the first chamber is a left ventricle and the second chamber is a left atrium, and the porous covering is configured to promote tissue ingrowth such that regurgitant blood flow through the device from the left ventricle to the left atrium is reduced from 15% to 30% of a left ventricle stroke volume of the left ventricle at the time the device is implanted, to 0% to 20% of a left ventricle stroke volume of the left ventricle over a time period of one month to six months.

The foregoing and other objects, features, and advantages of the disclosed technology will become more apparent from the following detailed description, which proceeds with reference to the accompanying figures.

BRIEF DESCRIPTION OF THE DRAWINGS

FIG. 17 is a side elevation view of a proximal end portion of the delivery apparatus of FIG. 11.

FIG. 18 is a cross-sectional view of the proximal end portion of the delivery apparatus of FIG. 11, taken along the line 18-18 shown in FIG. 17.

DETAILED DESCRIPTION

Figure 1:
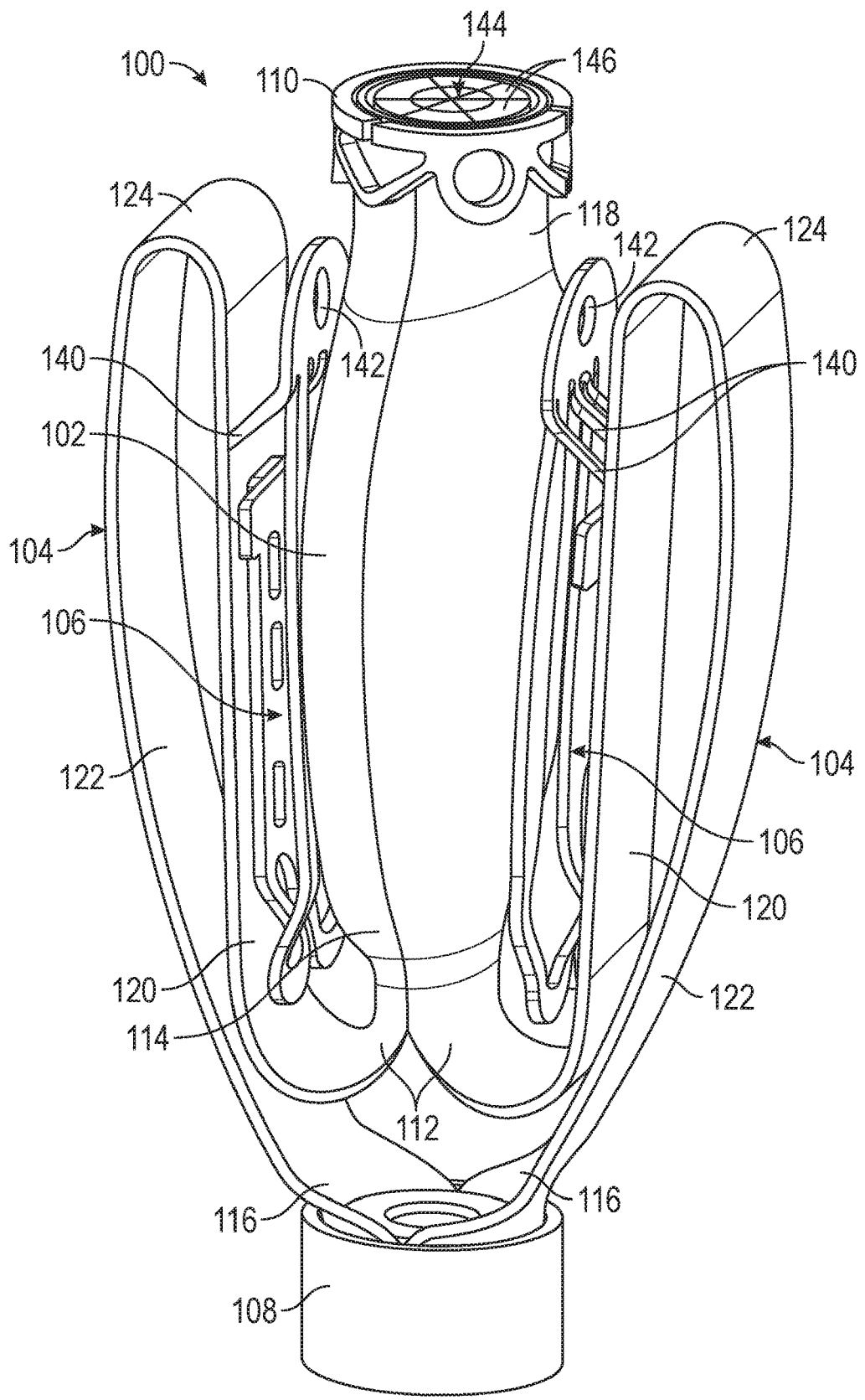
FIG. 1 illustrates an exemplary embodiment of a prosthetic spacer device, showing a first configuration.

Described herein are embodiments of prosthetic spacer devices that are primarily intended to be implanted at one of the mitral, aortic, tricuspid, or pulmonary valve regions of a human heart, as well as devices and methods for implanting the same. The prosthetic spacer devices can be used to help restore and/or replace the functionality of a defective native valve.

Existing prosthetic spacer devices are typically configured to reduce or prevent valvular regurgitation immediately upon implantation in a heart valve, and particularly in the mitral valve. For example, in a typical configuration, a prosthetic spacer device can include a central or main body and one or more movable elements configured to capture the leaflets of the native valve between the elements and the main body. The native leaflets can thereby form a seal against the main body. The main body, in turn, can be configured to prevent blood flow through the prosthetic device such that an acute reduction in mitral regurgitation is achieved at the time of implantation. This can be advantageous in patients where left ventricular function is not severely degraded. For example, immediate reduction of mitral regurgitation upon implantation of the device can be acceptable where the patient has a left ventricle ejection fraction (LVEF) of greater than 20% of the volume of the left ventricle. As used herein, "left ventricle ejection fraction" and the abbreviation "LVEF" refer to the fraction of the end-diastolic volume of the left ventricle that is ejected from the left ventricle during ventricular systole.

However, in patients with LVEF less than 20%, an acute reduction in mitral regurgitation upon implantation of the prosthetic spacer device can result in significant stress on the left ventricle, potentially resulting in heart failure. For example, in patients with moderate-to-severe or severe mitral regurgitation graded at 3+ or 4+ according to the methods and guidelines defined by the American Society of Echocardiography, a sudden reduction of mitral regurgitation graded at MR>3+ or MR>4+ to mitral regurgitation graded at MR≤2+ can result in heart failure and/or death. Accordingly, embodiments of a prosthetic spacer device are provided herein that provide for significant acute mitral regurgitation through the device upon implantation. The devices can be configured to slowly reduce mitral regurgitation over a time period of, for example, days, weeks, or months. This can reduce the stress on the left ventricle associated with a sudden reduction in mitral regurgitation. As used herein, reference to "mitral regurgitation" or "MR" graded at, e.g., 1+, 2+, 3+, or 4+ refers to the angiographic grading guidelines provided by the American Society of Echocardiography using assessment techniques including, for example, echocardiography, color flow Doppler, fluoroscopy, etc. (Zoghbi et al., ASE Guidelines and Standards: Recommendations for Noninvasive Evaluation of Native Valvular Regurgitation—A Report from the American Society of Echocardiography Developed in Collaboration with the Society for Cardiovascular Magnetic Resonance, Journal of the American Society of Echocardiography, April 2017).

Embodiments of prosthetic spacer devices described herein can comprise a spacer member and at least one anchor. In certain embodiments, the prosthetic spacer devices can further comprise at least one clasp and at least one collar. The spacer member can be configured to be positioned within the native valve orifice to fill a space between improperly functioning native leaflets that do not naturally coapt completely. In certain examples, the spacer member can be configured to allow acute regurgitation through the prosthetic device when the device is implanted, and to reduce regurgitation through the device gradually (e.g., as the implant endothelializes). In such examples, the spacer member can be configured to provide a flow path through the prosthetic device for retrograde blood flow (e.g., from the left ventricle to the left atrium during ventricular systole). Examples of other prosthetic spacer devices are described further in U.S. application Ser. No. 15/973,892 filed May 8, 2018, which is incorporated herein by reference. The spacer member can have various shapes. In some embodiments, the spacer member can have an elongated cylindrical shape having a round cross-sectional shape. In other embodiments, the spacer member can have an ovular cross-sectional shape, a crescent cross-sectional shape, or various other non-cylindrical shapes.

In certain embodiments configured for implantation in a native mitral valve, the spacer member can have an atrial or upper end positioned in or adjacent to the left atrium of the heart, a ventricular or lower end positioned in or adjacent to the left ventricle of the heart, and an annular side surface that extends between the native mitral leaflets.

The anchor can be configured to secure the prosthetic spacer device to one or more of the native leaflets such that the spacer member is positioned between the native leaflets. The anchor can be configured to be positioned behind a native leaflet when implanted such that the native leaflet is captured between the anchor and the spacer member.

Figure 2:
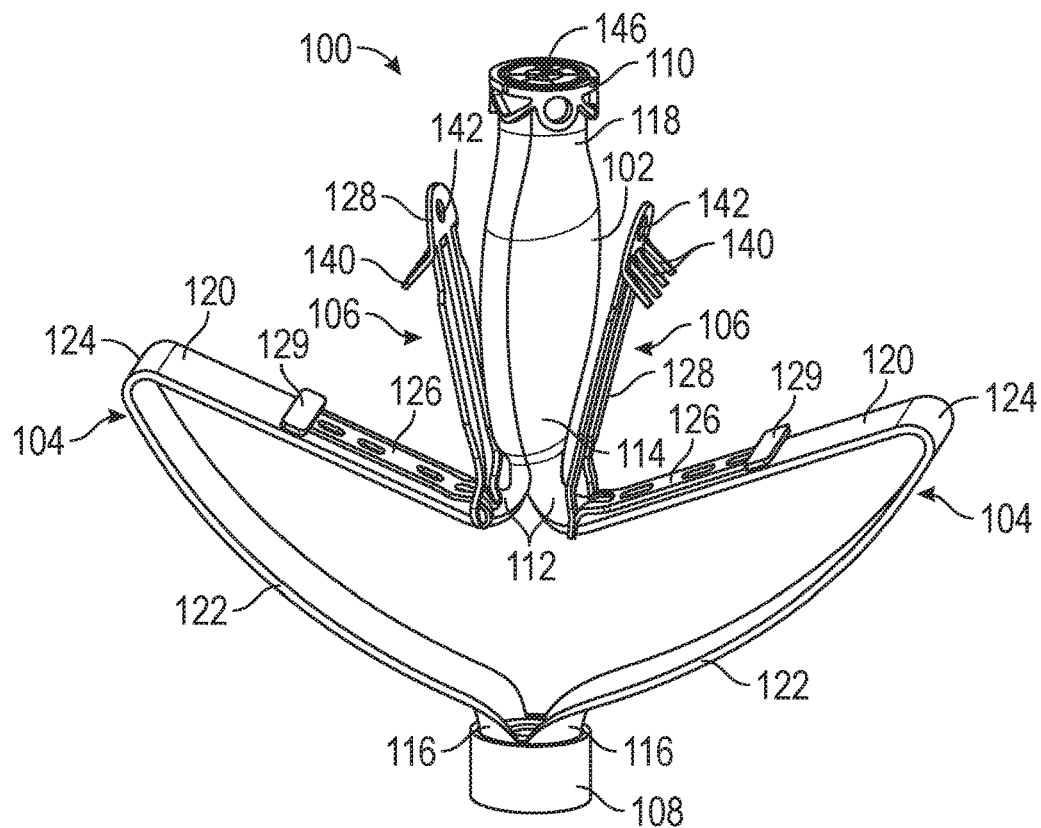
FIG. 2 is a perspective view of the prosthetic spacer device of FIG. 1, showing a second configuration.
Figure 3:
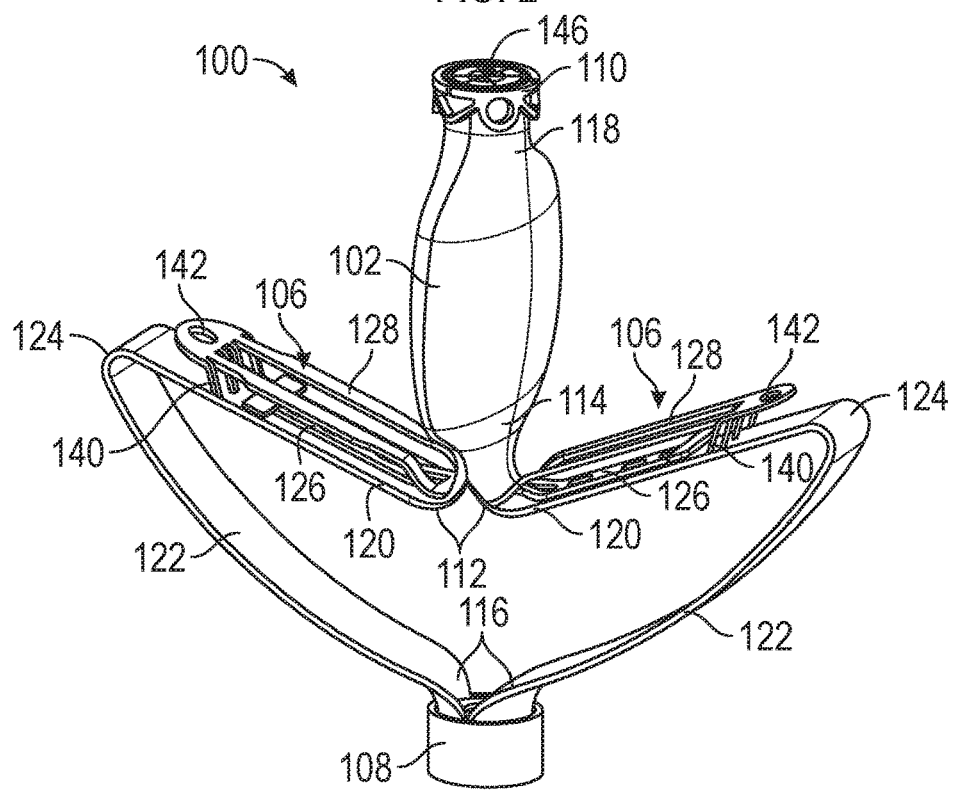
FIG. 3 is a perspective view of the prosthetic spacer device of FIG. 1, showing a third configuration.

FIGS. 1-5 show an exemplary embodiment of a prosthetic spacer device 100 and its components. Referring to FIG. 1, the prosthetic spacer device 100 can comprise a spacer member 102, a plurality of anchors or paddles 104 (e.g., two in the illustrated embodiment), a plurality of clasps 106 (e.g., two in the illustrated embodiment), a first collar 108, and a second collar 110. As best shown in FIG. 3, first end portions 112 of the anchors 104 can be coupled to and extend from a first end portion 114 of the spacer member 102, and second end portions 116 of the anchors 104 can be coupled to the first collar 108. The second collar 110 can be coupled to a second end portion 118 of the spacer member 102.

The spacer member 102 and the anchors 104 can be coupled together in various ways. For example, as shown in the illustrated embodiment, the spacer member 102 and the anchors 104 can be coupled together by integrally forming the spacer member 102 and the anchors 104 as a single, unitary component. This can be accomplished, for example, by forming the spacer member 102 and the anchors 104 from a braided or woven material, such as braided or woven nitinol wire, as described in greater detail below with reference to FIG. 8A. Thus, although in practice the spacer member and the anchors may be made from braided and/or woven wire, these features are illustrated schematically as solid members in FIGS. 1-3 for purposes of illustration. In other embodiments, the spacer member 102 and the anchors 104 can be coupled together by welding, fasteners, adhesive, and/or other means for coupling.

Referring to FIG. 2, the anchors 104 can comprise first portions 120 and second portions 122 separated by joint portions 124. In this manner, the anchors 104 are configured similar to legs in that the first portions 120 are like upper portions of the legs, the second portions 122 are like lower portions of the legs, and the joint portions 124 are like knee portions of the legs.

The anchors 104 can be configured to move between various configurations by axially moving the first collar 108 and thus the anchors 104 relative to the spacer member 102 along a longitudinal axis extending between the first and second end portions 114, 118 of the spacer member 104. For example, the anchors 104 can be positioned in a straight configuration by moving the first collar 108 away from the spacer member 102 such that the anchors 104 are taut. In the straight configuration, the joint portions 124 of the anchors 106 are adjacent the longitudinal axis of the spacer member 102 (e.g., similar to the configuration shown in FIG. 20).

From the straight configuration, the anchors 104 can be moved to a fully folded configuration (e.g., FIG. 1) by moving the first collar 108 toward the spacer member 102. Initially as the first collar 108 moves toward the spacer member 102, the anchors 104 bend at the joint portions 124, and the joint portions 124 move radially outwardly relative to the longitudinal axis of the spacer member 102 and axially toward the first end portion 114 of the spacer member 102, as shown in FIGS. 2-3. As the first collar 108 continues to move toward the spacer member 102, the joint portions 124 move radially inwardly relative to the longitudinal axis of the spacer member 102 and axially toward the second end portion 118 of the spacer member 102, as shown in FIG. 1.

In some embodiments, an angle between the first portions 120 of the anchors 104 and the spacer member 102 can be approximately 180 degrees when the anchors 104 are in the straight configuration (see, e.g., FIG. 20), and the angle between the first portions 120 of the anchors 104 and the spacer member 102 can be approximately 0 degrees when the anchors 104 are in the fully folded configuration. The anchors 104 can be positioned in various partially folded configurations such that the angle between the first portions 120 of the anchors 104 and the spacer member 102 can be approximately 10-170 degrees or approximately 45-135 degrees.

Configuring the prosthetic spacer device 100 such that the anchors 104 can extend to a straight or approximately straight configuration (e.g., approximately 120-180 degrees relative to the spacer member 102) can provide several advantages. For example, this can reduce the radial crimp profile of the prosthetic spacer device 100. It can also make it easier to capture the native leaflets by providing a larger opening in which to capture the native leaflets. Additionally, the relatively narrow, straight configuration can prevent or reduce the likelihood that the prosthetic spacer device 100 will become entangled in native anatomy (e.g., chordae tendineae) when positioning and/or retrieving the prosthetic spacer device 100 into the delivery apparatus.

Referring again to FIG. 2, the clasps 106 can comprise attachment portions 126 and arm portions 128. The attachment portions 126 can be coupled to the first portions 120 of the anchors 104 in various ways such as with sutures, adhesive, fasteners (e.g., plates 129), welding and/or means for coupling.

The arm portions 128 can pivot relative to the attachment portions 126 between an open configuration (e.g., FIG. 2) and a closed configuration (FIGS. 1 and 3). In some embodiments, the clasps 106 can be biased to the closed configuration. In the open configuration, the attachment portions 126 and the arm portions 128 pivot away from each other such that native leaflets can be positioned between the attachment portions 126 and the arm portions 128. In the closed configuration, the attachment portions 126 and the arm portions 128 pivot toward each other, thereby clamping the native leaflets between the attachment portions 126 and the arm portions 128.

Figure 4:
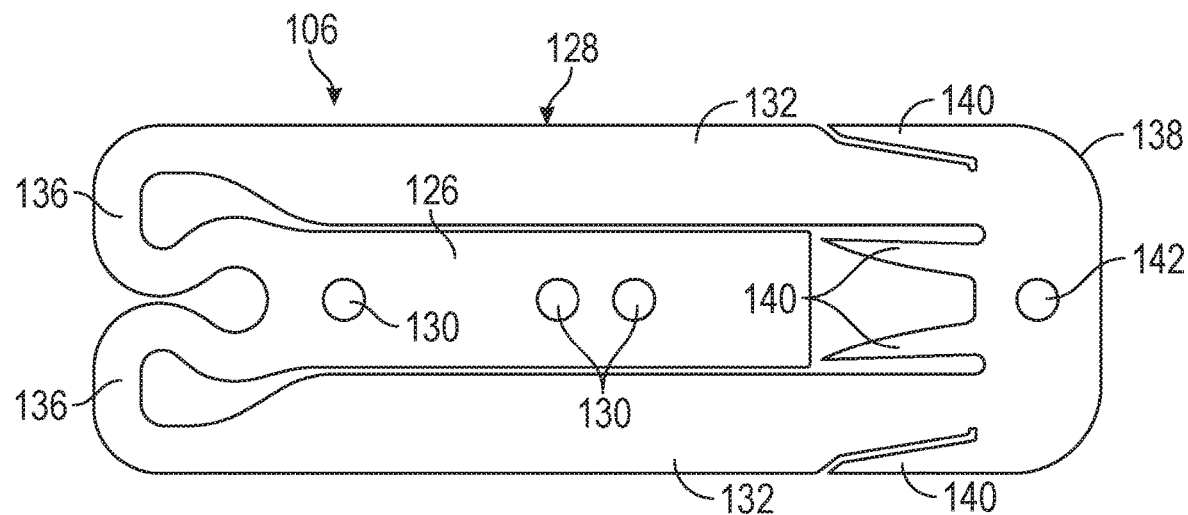
FIG. 4 is a plan view of a clasp of the prosthetic spacer device of FIG. 1, showing a first configuration.
Figure 5:
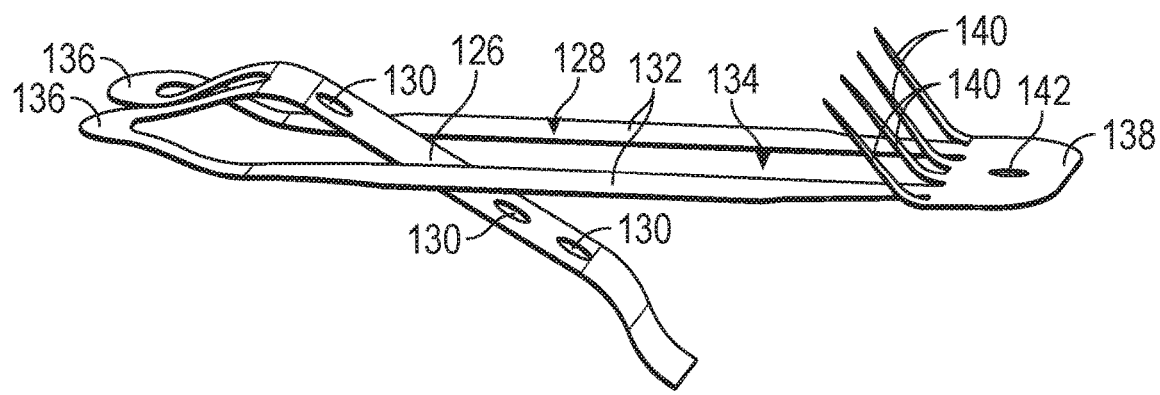
FIG. 5 is a perspective view of the clasp of the prosthetic spacer device of FIG. 1, showing a second configuration.

Referring to FIGS. 4-5, the attachment portions 126 (only one shown in FIGS. 4-5) can comprise one or more openings 130 (e.g., three in the illustrated embodiment). At least some of the openings 130 can be used to couple the attachment portions 126 to the anchors 104. For example, sutures and/or fasteners can extend through the openings 130 to couple the attachment portions 126 to the anchors 104.

The arm portions 128 can comprise a plurality of side beams 132 that are spaced apart to form slots 134. The slots 134 can be configured to receive the attachment portions 126. The arm portions 128 can also include fixed end portions 136 that are coupled to the attachment portions 126 and free end portions 138 disposed opposite the fixed end portions 138.

The free end portions 138 can comprise gripper elements such as barbs 140 and/or other means for frictionally engaging native leaflet tissue. The gripper elements can be configured to engage and/or penetrate the native leaflet tissue to help retain the native leaflets between the attachment portions 126 and arm portions 128 of the clasps 106.

The free end portions 138 can also comprise eyelets 142, which can be used to couple the free end portions 138 to an actuation mechanism configured to pivot the arm portions 128 relative to the attachment portions 126. Additional details regarding coupling the clasps 106 to the actuation mechanism are provided below.

In some embodiments, the clasps 106 can be formed from a shape memory material such as nitinol, stainless steel, and/or shape memory polymers. In certain embodiments, the clasps 106 can be formed by laser-cutting a piece of flat sheet of material (e.g., nitinol) in the configuration shown in FIG. 4 and then shape-setting the clasp 106 in the configuration shown in FIG. 5.

Shape-setting the clasps 106 in this manner can provide several advantages. For example, the clasps 106 can be compressed from the shape-set configuration (e.g., FIG. 5) to the flat configuration (e.g., FIG. 4), which reduces the radial crimp profile of the clasps 106. Also, this also improves trackability and retrievability of the prosthetic spacer device 100 relative to a catheter shaft of a delivery apparatus because barbs 140 are pointing radially inwardly toward the anchors 104 when the prosthetic spacer device 100 is advanced through or retrieved into the catheter shaft (see, e.g., FIG. 20). This thus prevents or reduces the likelihood that the clasps 106 may snag or skive the catheter shaft.

In addition, shape-setting the clasps 106 in the configuration shown in FIG. 5 can increase the clamping force of the clasps 106 when the clasps 106 are in the closed configuration. This is because the arm portions 128 are shape-set relative to the attachment portions 126 to a first position (e.g., FIG. 5) which is beyond the position the arm portions 128 can achieve when the clasps 106 are attached to the anchors 104 (e.g., FIG. 3) because the anchors 104 prevent the arm portions 128 from further movement toward the shape-set configuration. This results in arm portions 128 having a preload (i.e., the clamping force is greater than zero) when the clasps 106 are attached to the anchors 104 and in the closed configuration. Thus, shape-setting the clasps 106 in the FIG. 5 configuration can increase the clamping force of the clasps 106 compared to clasps that are shape-set in the closed configuration.

The magnitude of the preload of the clasps 106 can be altered by adjusting the angle in which the arm portions 128 are shape-set relative to the attachment portions 126. For example, increasing the relative angle between the arm portions 128 and the attachment portions 126 increases the preload, and decreasing the relative angle between the arm portions 128 and the attachment portions 126 decreases the preload.

In some embodiments, the second collar 110 and/or the spacer member 102 can comprise a hemostatic seal 144 configured to reduce or prevent blood from flowing through the second collar 110 and/or the spacer member 102. For example, in some embodiments, the hemostatic seal 144 can comprise a plurality of flexible flaps 146, as shown in FIG. 1. The flaps 146 can be configured to pivot from a sealed configuration to an open configuration to allow a delivery apparatus to extend through the second collar 110. When the delivery apparatus is removed, the flaps 146 can be configured to return to the sealed configuration from the open configuration. In other embodiments, the device need not include such a seal.

FIGS. 6-8B show an exemplary embodiment of a prosthetic spacer device 200. The prosthetic spacer device 200 can comprise a spacer member 202, a plurality of anchors 204, a plurality of clasps 206, a first collar 208, and a second collar 210. These components of the prosthetic spacer device 200 can be configured substantially similar to the corresponding components of the prosthetic spacer device 100.

Figure 6:
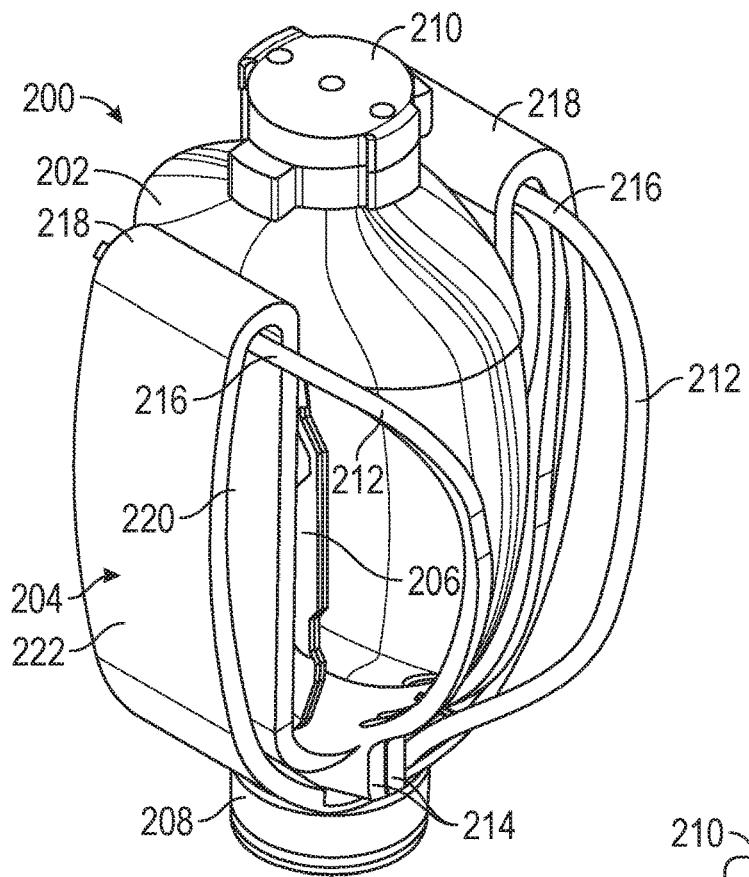
FIG. 6 illustrates another exemplary embodiment of a prosthetic spacer device.
Figure 7:
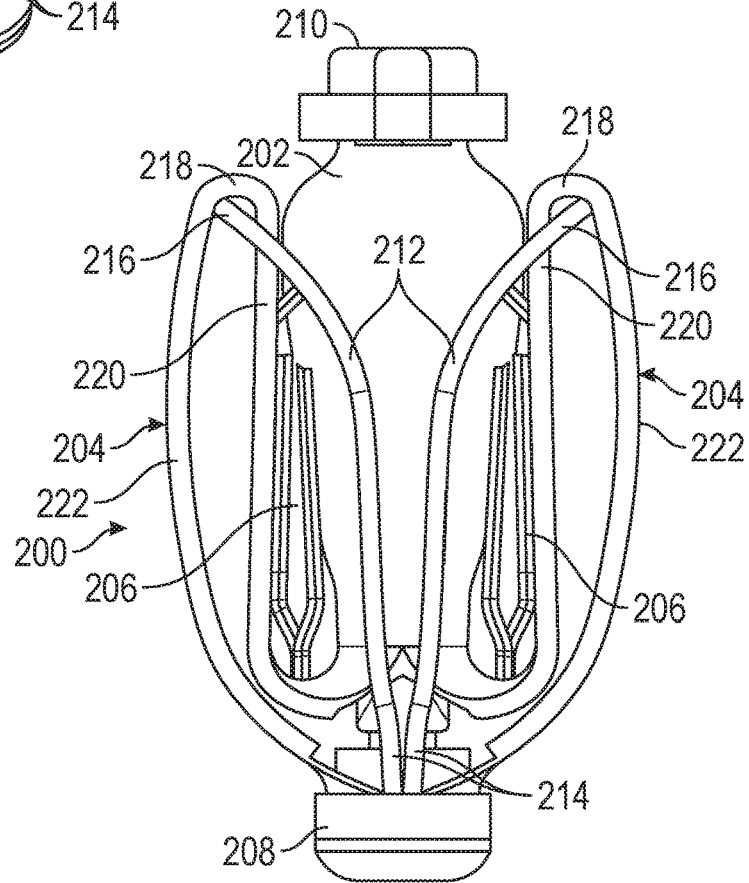
FIG. 7 is a side elevation view of the prosthetic spacer device of FIG. 6.

The prosthetic spacer device 200 can also include a plurality of anchor extension members 212. The anchor extension members 212 can be configured as loops with first end portions 214 coupled to and extending from the first collar 208 and second end portions 216 disposed opposite the first end portions 214. The anchor extension members 212 can be configured to extend circumferentially farther around the spacer member 202 than the anchors 204. For example, in some embodiments, each of the anchor extension members 216 can extend around approximately half the circumference of the spacer member 202 (as best shown in FIG. 7), and the anchors 204 can extend around less than half of circumference of the spacer member 202 (as best shown in FIG. 6). The anchor extension members 216 can also be configured to extend laterally (i.e., perpendicular to a longitudinal axis of the spacer member 202) beyond an outer diameter of the spacer member 202.

The anchor extension members 212 can further be configured such that free end portions 216 of the anchor extension members 212 are disposed axially adjacent a joint portion 218 of the anchors 204 and radially between first and second portions 220, 222 of the anchors 206 when the prosthetic spacer device 200 is in a folded configuration (e.g., FIGS. 6-8).

Configuring the anchor extension members 212 in this manner provides increased surface area compared to the anchors 204 alone. This can, for example, make it easier to capture and secure the native leaflets. The increased surface area can also distribute the clamping force of the anchors 204 and anchor extension members 212 against the native leaflets over a relatively larger surface of the native leaflets in order to further protect the native leaflet tissue.

The increased surface area of the anchor extension members 212 can also allow the native leaflets be to clamped to the prosthetic spacer device 200 such that the native leaflets coapt together at a location adjacent the prosthetic spacer device 200, as opposed to against the spacer member 202. This can, for example, improve the sealing of the native leaflets and contribute to an eventual reduction in mitral regurgitation.

Figure 8A:
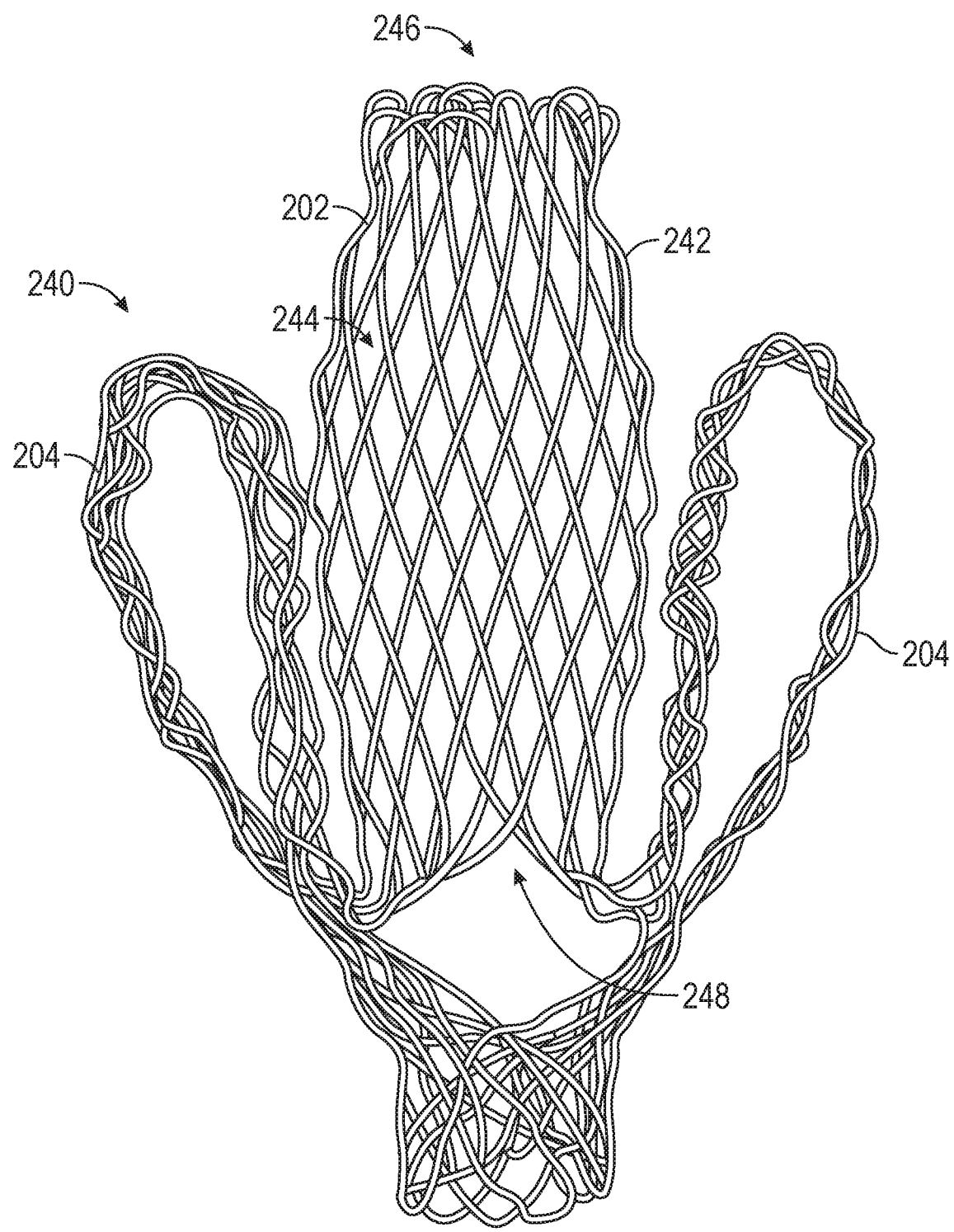
FIG. 8A is a side elevation view of a wire mesh structure of the prosthetic spacer device of FIG. 6.

As mentioned above, elements of the prosthetic spacer devices described herein, such as the spacer member and/or the anchor members, can be made from a porous structure such as a woven and/or braided wire mesh. FIG. 8A illustrates a representative embodiment of such a mesh structure 240 comprising a plurality of filaments or wires 242. In the embodiment of FIG. 8A, the wires 242 can be braided together to form the ovoid shape of the spacer member 202 such that the mesh structure defines a plurality of openings 244 around substantially the entire surface of the spacer member. The spacer member 202 can also define respective top and bottom central openings 246, 248 leading into the interior of the spacer member. The wires 242 can be woven together to form the anchors 204.

Figure 8B:
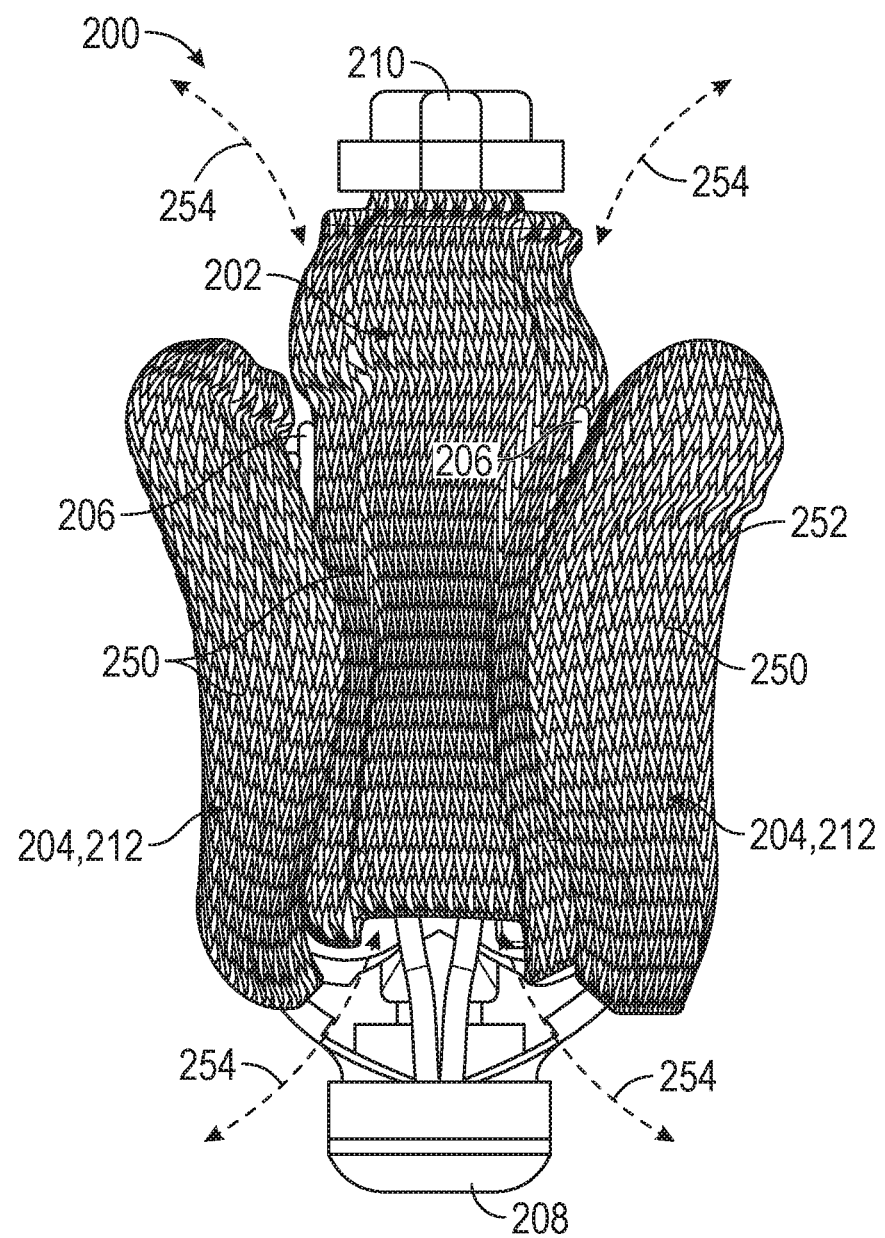
FIG. 8B is a side elevation view of the prosthetic spacer device of FIG. 6, showing a cover on the wire mesh structure of FIG. 8A.

FIG. 8B illustrates the assembled device 200 including a covering 250 disposed about the spacer member 202 and the anchors 204. In some examples, the covering 250 can be porous such that the covering is permeable to blood flow. For example, in the illustrated embodiment, the covering 250 can be an openwork fabric or netting defining a plurality of openings generally indicated at 252. In certain examples, the covering 250 can comprise a low-density knitted polyester fabric having, for example, 60-120 courses per inch and 20-60 wales per inch. The covering 250 can also comprise any of various woven fabrics such as velour, non-woven fabrics such as felt or gauze, or any of various porous or blood-permeable polymeric materials, such as expanded polytetrafluorethylene (ePTFE), polyethylene terephthalate (PET), ultra-high molecular weight polyethylene (UHMWPE), etc.

In certain examples, the covering 250 can be permeable to blood such that blood can flow through the covering 250, through the mesh structure 240, and into or out of the interior of the spacer member 202. In this manner, the spacer member 202 can provide a flow path through the prosthetic spacer device generally indicated by double-headed arrows 254. The direction of blood flow along the flow path 254 can be in a direction, for example, from a region of higher blood pressure to a region of lower blood pressure, such as from the left ventricle to the left atrium during ventricular systole. In certain examples, blood can also flow through the openings 246, 248. This can provide for acute regurgitant blood flow through the prosthetic spacer device and, in particular, through the spacer member 202, at the time the device is implanted, as described in greater detail below.

Figure 9:
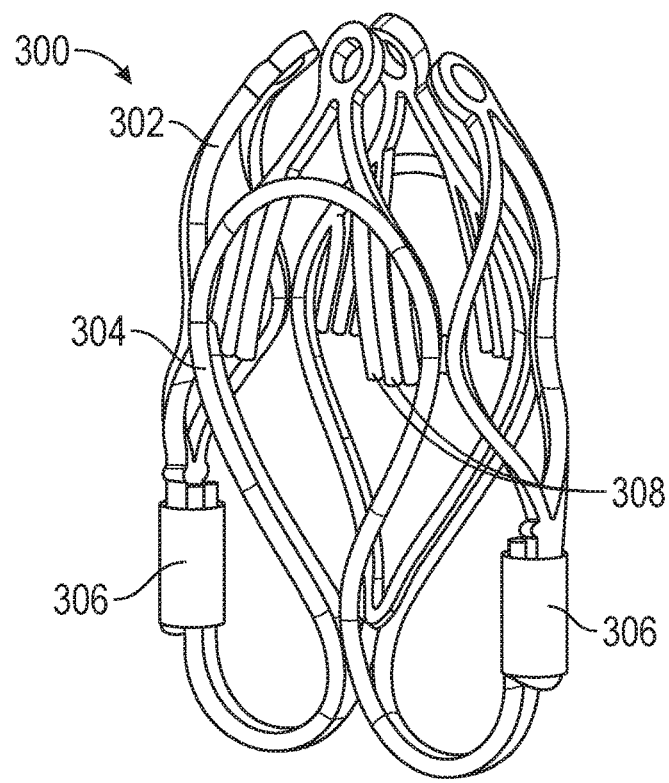
FIG. 9 illustrates another exemplary embodiment of a prosthetic spacer device.
Figure 10:
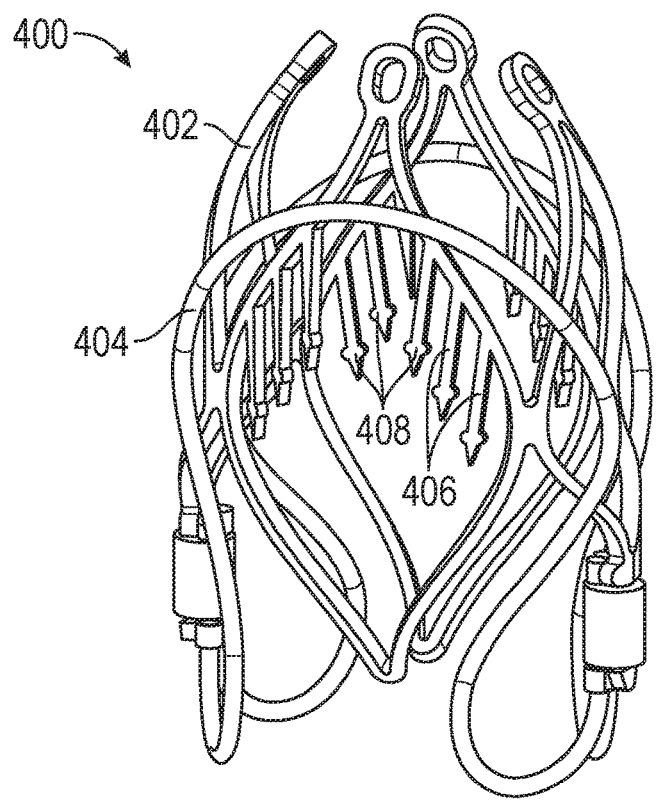
FIG. 10 illustrates another exemplary embodiment of a prosthetic spacer device.

FIGS. 9 and 10 illustrate other embodiments of prosthetic spacer devices that may be used in combination with the porous covering embodiments described above. FIG. 9 shows an exemplary embodiment of a prosthetic spacer device 300 comprising an annular spacer member 302 in the form of a metal frame, and anchors 304 extending from the spacer member 302. The ends of each anchor 304 can be coupled to respective struts of the spacer member 302 by respective sleeves 306 that can be crimped around the end portions of the anchors 306 and the struts of the spacer member 302. Mounted on the frame of the spacer member 302 can be one or more barbs or projections 308. The free ends of the projections 308 can comprise various shapes including rounded, pointed, barbed, etc. The projections 308 can exert a retaining force against native leaflets by virtue of the anchors 304, which are shaped to force the native leaflets inwardly into the spacer member 302 in the area below the free ends of the anchors 304. The device 300 can include a porous covering in order to allow blood flow through the spacer member 302, as described above.

FIG. 10 shows another embodiment of a prosthetic spacer device 400. The prosthetic spacer device 400 can comprise an annular spacer member 402 in the form of a metal frame and anchors 404 extending from the spacer member 402 similar to the prosthetic spacer device 300. The anchors 404 of the prosthetic spacer device 400 can be configured similar to the anchors 304 of the prosthetic spacer device 300 except that the curve at the free end of each anchor 404 comprises a larger radius than the anchors 304. As such, the anchors 404 cover a relatively larger portion of the spacer member 402 than the anchors 304. This can, for example, distribute the clamping force of the anchors 404 against the native leaflets over a relatively larger surface of the native leaflets in order to further protect the native leaflet tissue. It can also improve sealing because the native leaflets are clamped against the prosthetic spacer device 400 such that the native leaflets coapt together at a location adjacent the prosthetic spacer device 400, as opposed to against the spacer member 402.

Also, mounted on the frame of the spacer member 402 can be one or more barbs or projections 406. The free ends of the projections 406 can comprise stoppers 408 configured to limit the extent of the projections 406 that can engage and/or penetrate the native leaflets. The device 400 can also include a porous covering in order to allow blood flow through the spacer member 402, as described above.

Additional details regarding the prosthetic spacer devices can be found, for example, in U.S. Patent Application Publication No. 2016/0331523, which is incorporated by reference herein.

Figure 11:
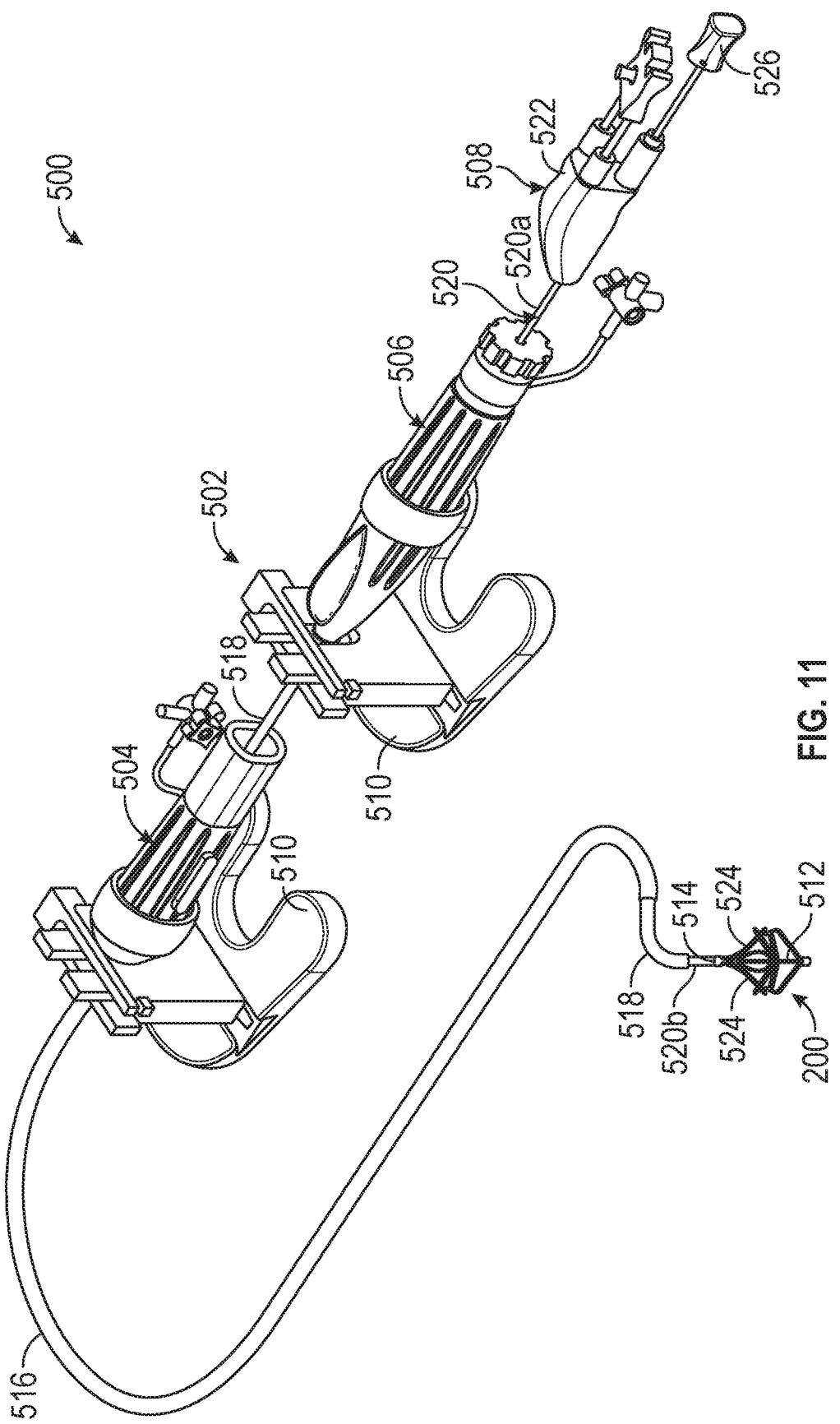
FIG. 11 illustrates an exemplary embodiment of a delivery assembly comprising the prosthetic spacer device of FIG. 6 (shown in partial cross-section) and a delivery apparatus.

The prosthetic spacer devices described herein can be coupled to a delivery apparatus to form a delivery assembly. The delivery apparatus can be used to percutaneously deliver, position, and/or secure the prosthetic spacer device within a patient's native heart valve region. FIGS. 11-27B show an exemplary delivery assembly 500 and its components. Referring to FIG. 11, the delivery assembly 500 can comprise the prosthetic spacer device 200 and a delivery apparatus 502. The delivery apparatus 502 can comprise a plurality of catheters and catheter stabilizers. For example, in the illustrated embodiment, the delivery apparatus 502 includes a first catheter 504, a second catheter 506, a third catheter 508, and catheter stabilizers 510. The second catheter 506 extends coaxially through the first catheter 504, and the third catheter 508 extends coaxially through the first and second catheters 504, 506. The prosthetic spacer device 200 can be releasably coupled to a distal end portion of the third catheter 508 of the delivery apparatus 502, as further described below.

In the illustrated embodiment, the delivery assembly 500 is configured, for example, for implanting the prosthetic spacer device 200 in a native mitral valve via a transseptal delivery approach. In other embodiments, the delivery assembly 500 can be configured for implanting the prosthetic spacer device 200 in aortic, tricuspid, or pulmonary valve regions of a human heart. Also, the delivery assembly 500 can be configured for various delivery methods, including transseptal, transaortic, transventricular, etc.

Figure 12A:
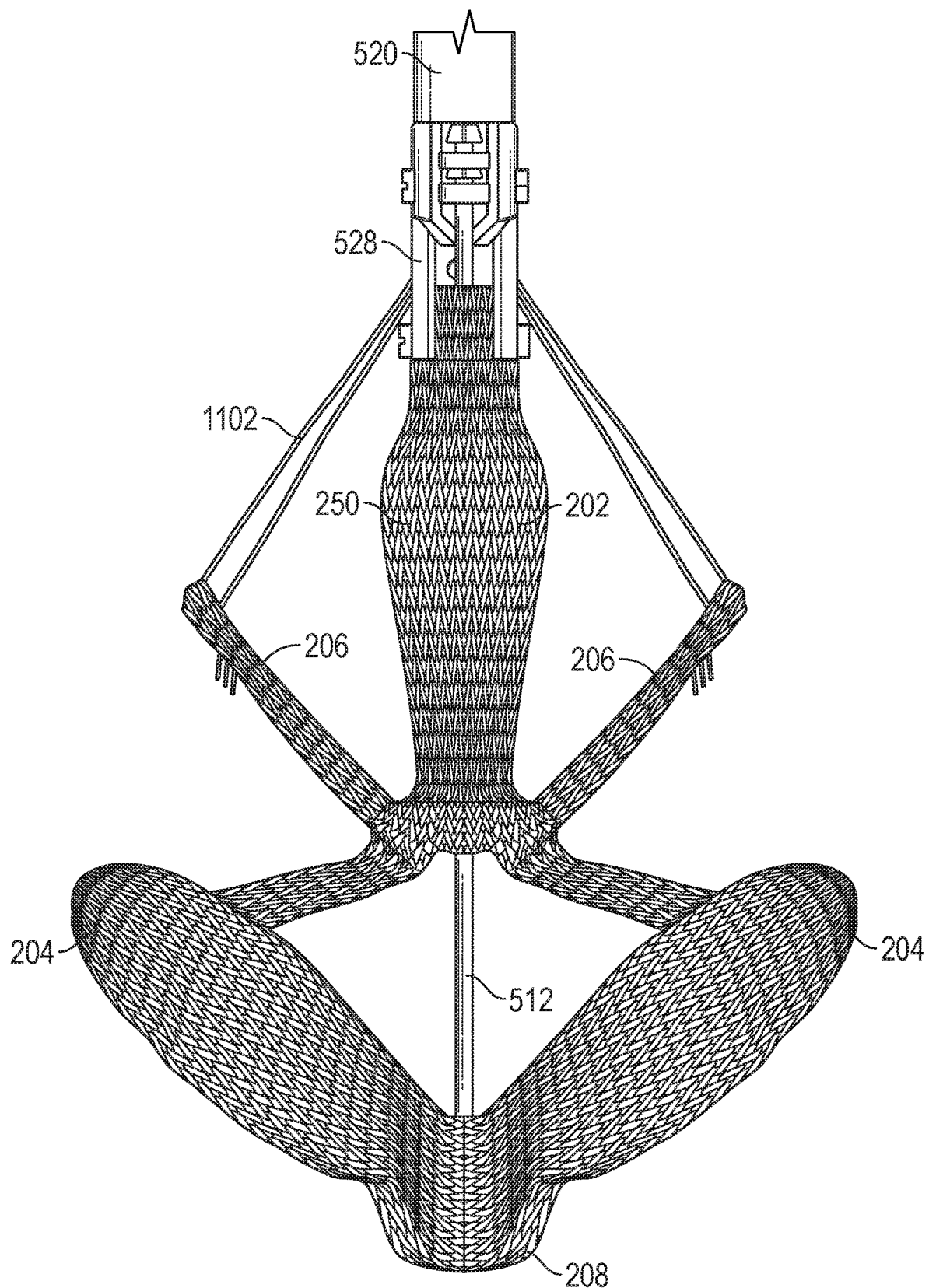
FIG. 12A is a side elevation view of the prosthetic spacer device of FIG. 6 coupled to the distal end portion of the delivery assembly of FIG. 11 with the anchors and clasps in the open configuration.
Figure 12B:
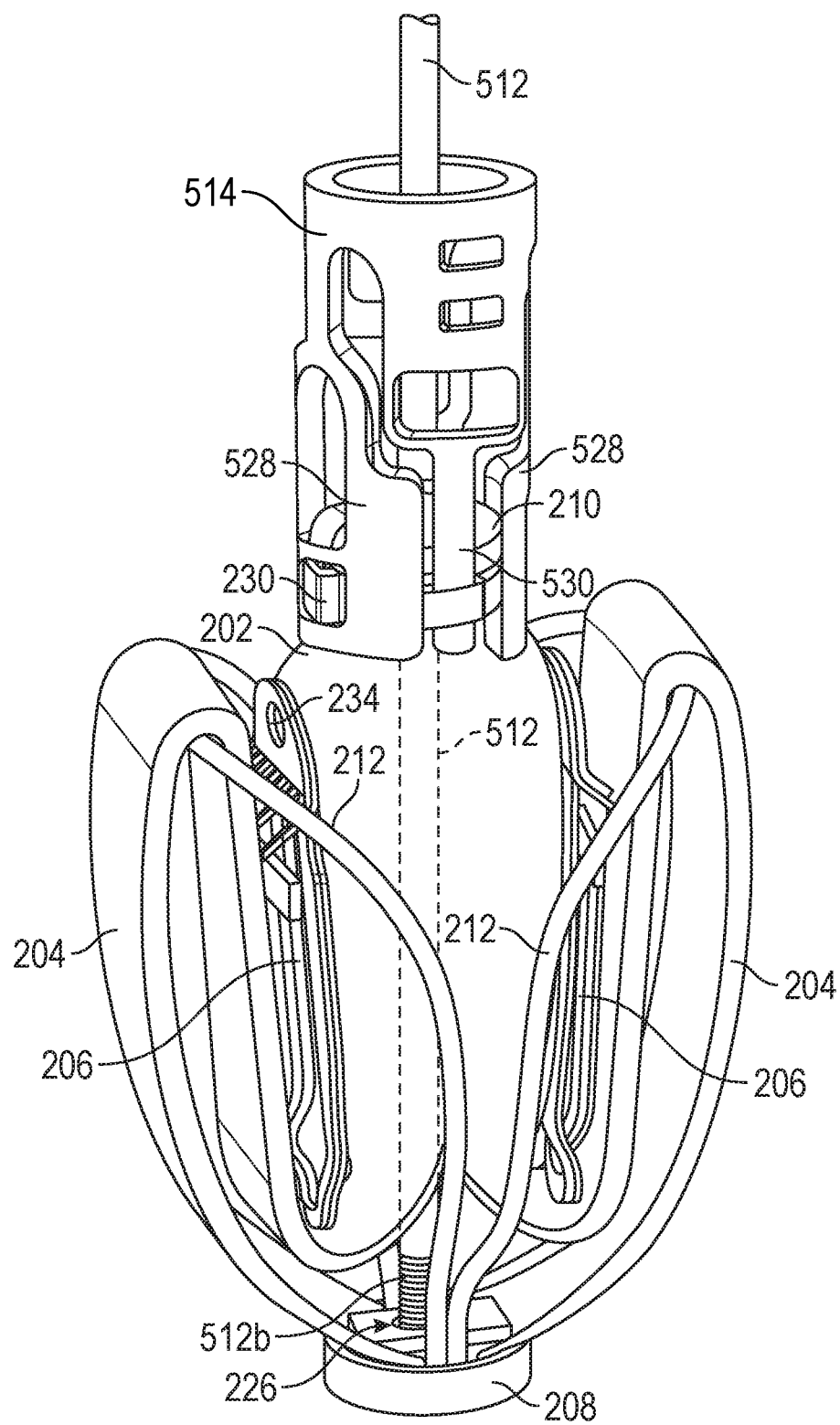
FIG. 12B is a perspective view of the distal end portion of the delivery assembly of FIG. 11, showing the prosthetic spacer device releasably coupled to the delivery apparatus with the anchors and clasps in the closed configuration and without the covering.
Figure 13:
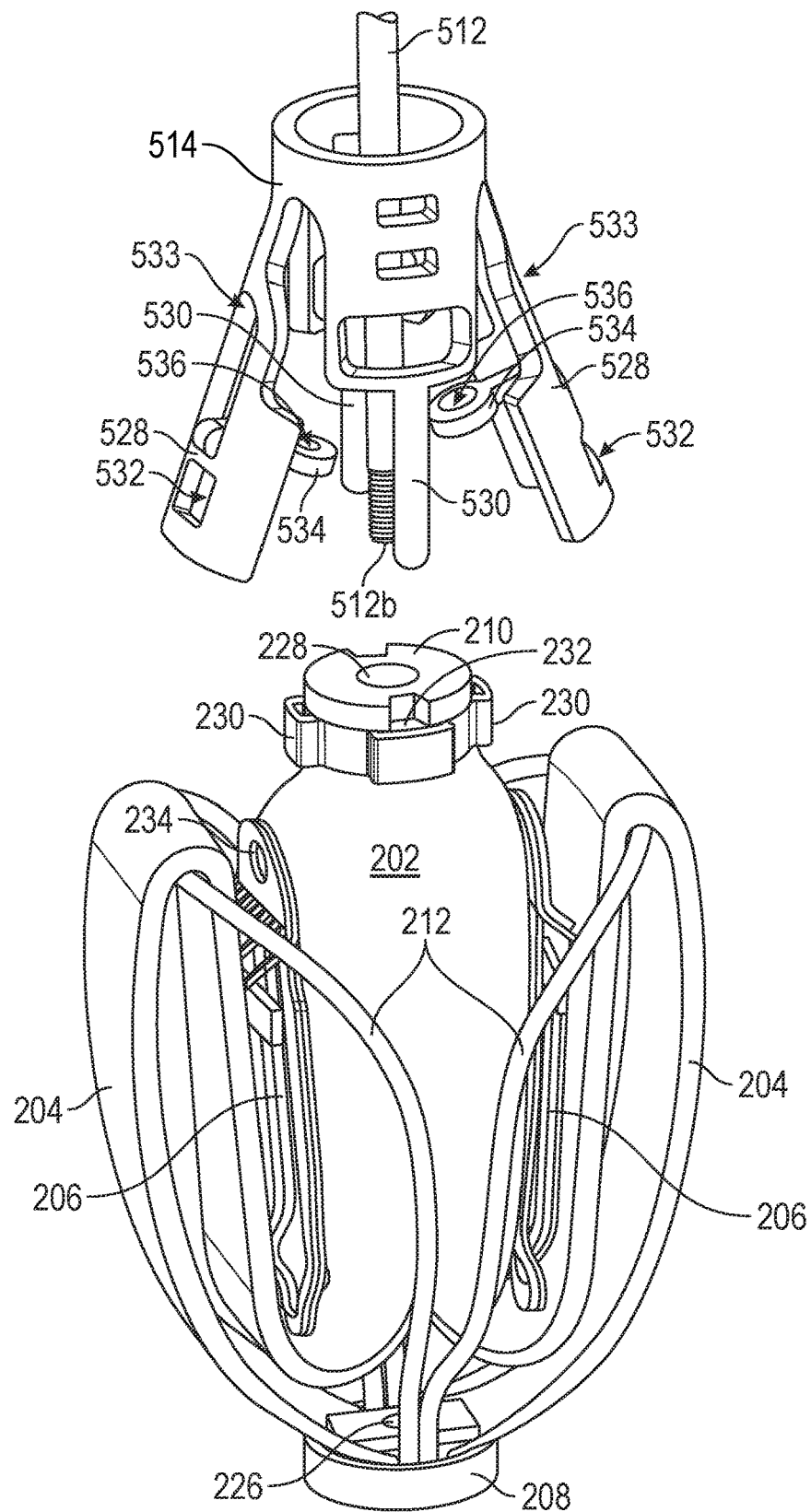
FIG. 13 is a perspective view of the distal end portion of the delivery assembly of FIG. 11, showing the prosthetic spacer device released from the delivery apparatus.

FIGS. 12A and 12B illustrate the prosthetic spacer device 200 coupled to the distal end of the delivery apparatus. In FIG. 12A, the spacer device 200 is shown in the open configuration and including the covering 250. In FIGS. 12B and 13, the spacer device 200 is shown without the covering 250, and with the spacer member 202 and the anchor members 204 schematically illustrated as solid members for purposes of illustration. Referring to FIG. 13, the first or distal collar 208 of the prosthetic spacer device 200 can include a bore 226. In some embodiments, the bore 226 can comprise internal threads configured to releasably engage corresponding external threads of an actuation shaft 512 of the delivery apparatus 502, as best shown in FIG. 12B.

Referring again to FIG. 13, the second or proximal collar 210 of the prosthetic spacer device 200 can include a central opening 228 that is axially aligned with the bore 226 of the distal collar 208. The central opening 228 of the proximal collar 210 can be configured to slidably receive the actuation shaft 512 of the delivery apparatus 502, as best shown in FIG. 12B. In some embodiments, the proximal collar 210 and/or the spacer member 202 can have a sealing member (not shown, but see, e.g., the sealing member 144 shown in FIG. 1) configured to seal the central opening 228 when the actuation shaft 512 is withdrawn from the central opening 228.

As best shown in FIG. 13, the proximal collar 210 can also include a plurality of bosses or projections 230 and a plurality of guide openings 232. The bosses 230 can extending radially outwardly and can be circumferentially offset (e.g., by 90 degrees) relative to the guide openings 232. The guide openings 232 can be disposed radially outwardly from the central opening 228. The projections 230 and the guide openings 232 of the proximal collar 210 can be configured to releasably engage a coupler 514 of the delivery apparatus 502, as shown in FIG. 12.

Referring again to FIG. 11 and as mentioned above, the delivery apparatus 502 can include the first and second catheters 504, 506. The first and second catheters 504, 506 can be used, for example, to access an implantation location (e.g., a native mitral valve region of a heart) and/or to position the third catheter 508 at the implantation location.

The first and second catheters 504, 506 can comprise first and second sheaths 516, 518, respectively. The catheters 504, 506 can be configured such that the sheaths 516, 518 are steerable. Additional details regarding the first catheter 504 can be found, for example, in U.S. Patent Application Publication No. U.S. 2016/0155987, which is incorporated by reference herein. Additional details regarding the second catheter 506 can be found, for example, in U.S. Publication No. 2018/0126124, which is incorporated by reference herein.

Referring still to FIG. 11, delivery apparatus 502 can also include the third catheter 508, as mentioned above. The third catheter 508 can be used, for example, to deliver, manipulate, position, and/or deploy the prosthetic spacer device 200 at the implantation location.

Figure 15:
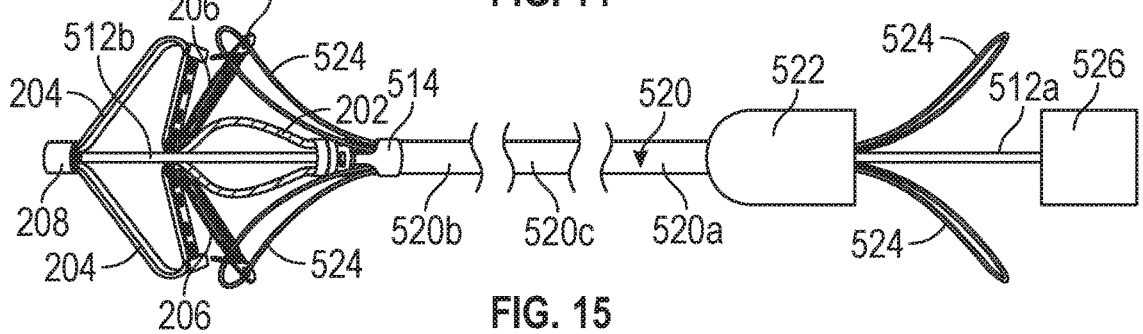
FIG. 15 is a perspective view of the delivery assembly of FIG. 11, with the prosthetic spacer device shown in partial cross-section and some components of the delivery apparatus shown schematically.

Referring to FIG. 15, the third catheter 508 can comprise the actuation or inner shaft 512, the coupler 514, an outer shaft 520, a handle 522 (shown schematically), and clasp control members 524. A proximal end portion 520a of the outer shaft 520 can be coupled to and extend distally from the handle 522, and a distal end portion 520b of the outer shaft 520 can be coupled to the coupler 514. A proximal end portion 512a of the actuation shaft 512 can coupled to an actuation knob 526. The actuation shaft 512 can extend distally from the knob 526 (shown schematically), through the handle 522, through the outer shaft 520, and through the coupler 514. The actuation shaft 512 can be moveable (e.g., axially and/or rotationally) relative to the outer shaft 520 and the handle 522. The clasp control members 524 can extend through and be axially movable relative to the handle 522 and the outer shaft 520. The clasp control members 524 can also be axially movable relative to the actuation shaft 512. In some embodiments, the clasp control members 524 can be configured as sutures, and can be looped through openings 234 in the clasps 206. In other embodiments, the clasp control members 524 can comprise sleeves 1102 through which connecting members and release members extend, as shown in FIG. 12A and further described in U.S. application Ser. No. 15/973,892 incorporated by reference above.

As best shown in FIGS. 12A, 12B, and 13, the actuation shaft 512 of the third catheter 508 can be releasably coupled to the distal collar 208 of the prosthetic spacer device 200. For example, in some embodiments, the distal end portion 512b of the actuation shaft 512 can comprise external thread configured to releasably engage the interior threads of the bore 226 of the prosthetic spacer device 200. As such, rotating the actuation shaft 512 in a first direction (e.g., clockwise) relative to the distal collar 208 of the prosthetic spacer device 200 releasably secures the actuation shaft 512 to the distal collar 208. Rotating the actuation shaft 512 in a second direction (e.g., counterclockwise) relative to the distal collar 208 of the prosthetic spacer device 200 releases the actuation shaft 512 from the distal collar 208.

Figure 14:
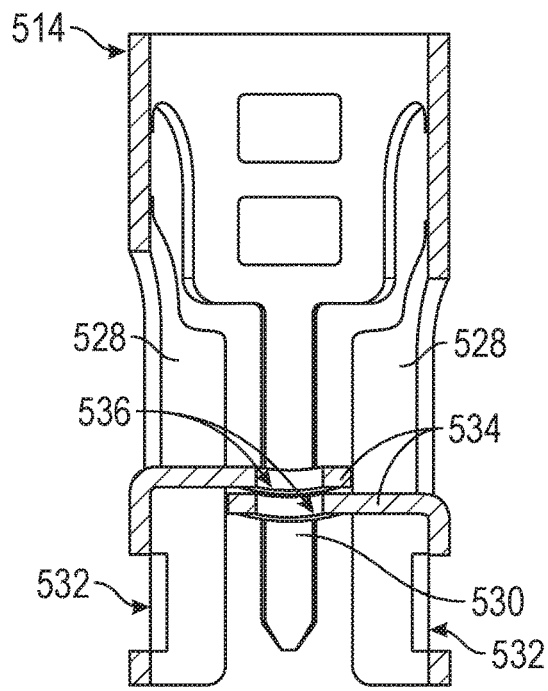
FIG. 14 is a cross-sectional view of a coupler of the delivery apparatus of FIG. 11.

Referring now to FIG. 12A-14, the coupler 514 of the third catheter 508 can be releasably coupled to the proximal collar 210 of the prosthetic spacer device 200. For example, in some embodiments, the coupler 514 can comprise a plurality of flexible arms 528 and a plurality of stabilizer members 530. The flexible arms 528 can comprise apertures 532, ports 533 (FIG. 13), and eyelets 534 (FIG. 14).

The flexible arms 528 can be configured to pivot between a first or release configuration (FIG. 13) and a second or coupled configuration (FIGS. 12B and 14). In the first configuration, the flexible arms 528 extend radially outwardly relative to the stabilizer members 530. In the second configuration, the flexible arms 530 extend axially parallel to the stabilizer members 530 and the eyelets 534 radially overlap, as best shown in FIG. 14. The flexible arms 528 can be configured (e.g., shape-set) so as to be biased to the first configuration.

The prosthetic spacer device 200 can be releasably coupled to the coupler 514 by inserting the stabilizer members 530 of the coupler 514 into the guide openings 232 of the prosthetic spacer device 200. The flexible arms 528 of the coupler 514 can then be pivoted radially inwardly from the first configuration to the second configuration such that the projections 230 of the prosthetic spacer device 200 extend radially into the apertures 532 of the flexible arms 528. The flexible arms 528 can be retained in the second configuration by inserting the distal end portion 512b of the actuation shaft 512 through openings 536 of the eyelets 534, which prevents the flexible arms 528 from pivoting radially outwardly from the second configuration to the first configuration, thereby releasably coupling the prosthetic spacer device 200 to the coupler 514.

The prosthetic spacer device 200 can be released from the coupler 514 by proximally retracting the actuation shaft 512 relative to the coupler 514 such that the distal end portion 512b of the actuation shaft 512 withdraws from the openings 536 of the eyelets 534. This allows the flexible arms 528 to pivot radially outwardly from the second configuration to the first configuration, which withdraws the projections 230 of the prosthetic spacer device 200 from the apertures 532 of the flexible arms 528. The stabilizer members 530 can remain inserted into the guide openings 232 of the prosthetic spacer device 200 during and after the flexible arms 528 are released. This can, for example, prevent the prosthetic spacer device 200 from moving (e.g., shifting and/or rocking) while the flexible arms 528 are released. The stabilizer members 530 can then be withdrawn from the guide openings 232 of the prosthetic spacer device 200 by proximally retracting the coupler 514 relative to the prosthetic spacer device 200, thereby releasing the prosthetic spacer device 200 from the coupler 514.

Referring to FIG. 15, the outer shaft 520 of the third catheter 508 can be an elongate shaft extending axially between the proximal end portion 520a, which is coupled the handle 522, and the distal end portion 520b, which is coupled to the coupler 514. The outer shaft 520 can also include an intermediate portion 520c disposed between the proximal and distal end portions 520a, 520b.

Figure 16:
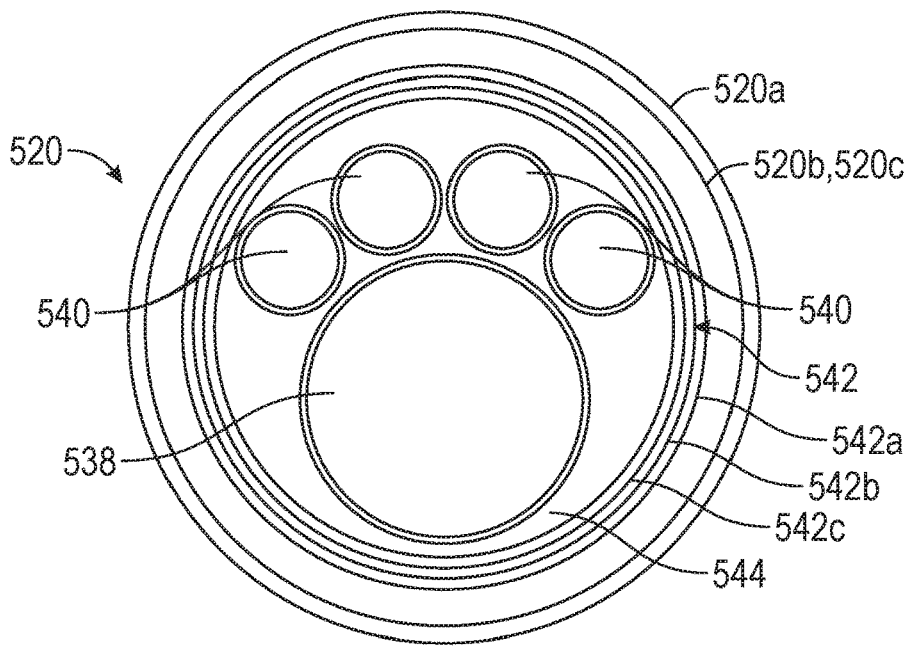
FIG. 16 is a plan view of a shaft of the delivery apparatus of FIG. 11.

Referring to FIG. 16, the outer shaft 520 can comprise a plurality of axially extending lumens, including an actuation shaft lumen 538 and a plurality of control member lumens 540 (e.g., four in the illustrated embodiment). In some embodiments, the outer shaft 520 can comprise more (e.g., six) or less (e.g., two) than four control member lumens 540.

The actuation shaft lumen 538 can be configured to receive the actuation shaft 512, and the control member lumens 540 can be configured to receive one or more clasp control members 524. The lumens 538, 540 can also be configured such that the actuation shaft 512 and clasp control members 524 can be movable (e.g., axially and/or rotationally) relative to the respective lumens 538, 540. In particular embodiments, the lumens 538, 540 can comprise a liner or coating configured to reduce friction within the lumens 538, 540. For example, the lumens 538, 540 can comprise a liner comprising PTFE.

Referring still to FIGS. 15-16, the outer shaft 520 can be formed from various materials, including metals and polymers. For example, in one particular embodiment, the proximal end portion 520a can comprise stainless steel and the distal and intermediate portions 520b, 520c can comprise PEBA (e.g., PEBAX®). The outer shaft 520 can also comprise an outer covering or coating, such as a polymer that is reflowed over the portions 520a, 520b, and 520c.

The outer shaft 520 can include one or more coil portions 542 disposed radially outwardly from the lumens 538, 540. For example, in one particular embodiment, the outer shaft 520 can comprise a first coil 542a, a second coil 542b, and a third coil 542c. The first coil 542a can be the radially outermost coil, the third coil 542c can be the radially innermost coil, and the second coil 542b can be radially disposed between the first coils 542a and the third coil 542c.

The coil portions 542 can comprise various materials and/or configurations. For example, the coil portions 542 can be formed from stainless steel. In one particular embodiment, the first and third coils 542a, 542c comprise stainless steel coils wound in a left hand configuration, and the second coil 542b comprises a stainless steel coil wound in a right hand configuration.

The coil portions 542 can also comprise various pitches. The pitch of one or more of the coils 542 can be the same or different than the pitch of one or more other coils 542. In one particular embodiment, the first and second coils 542a, 542b can have a first pitch (e.g., 0.74 in.), and the third coil can comprise a second pitch (e.g., 0.14 in.).

The outer shaft 520 can also comprise a tie layer 544 disposed radially inwardly from the third coil 542c. The tie layer 544 can be formed of various materials including polymers, such as PEBA (e.g., PEBAX®).

Figure 19:
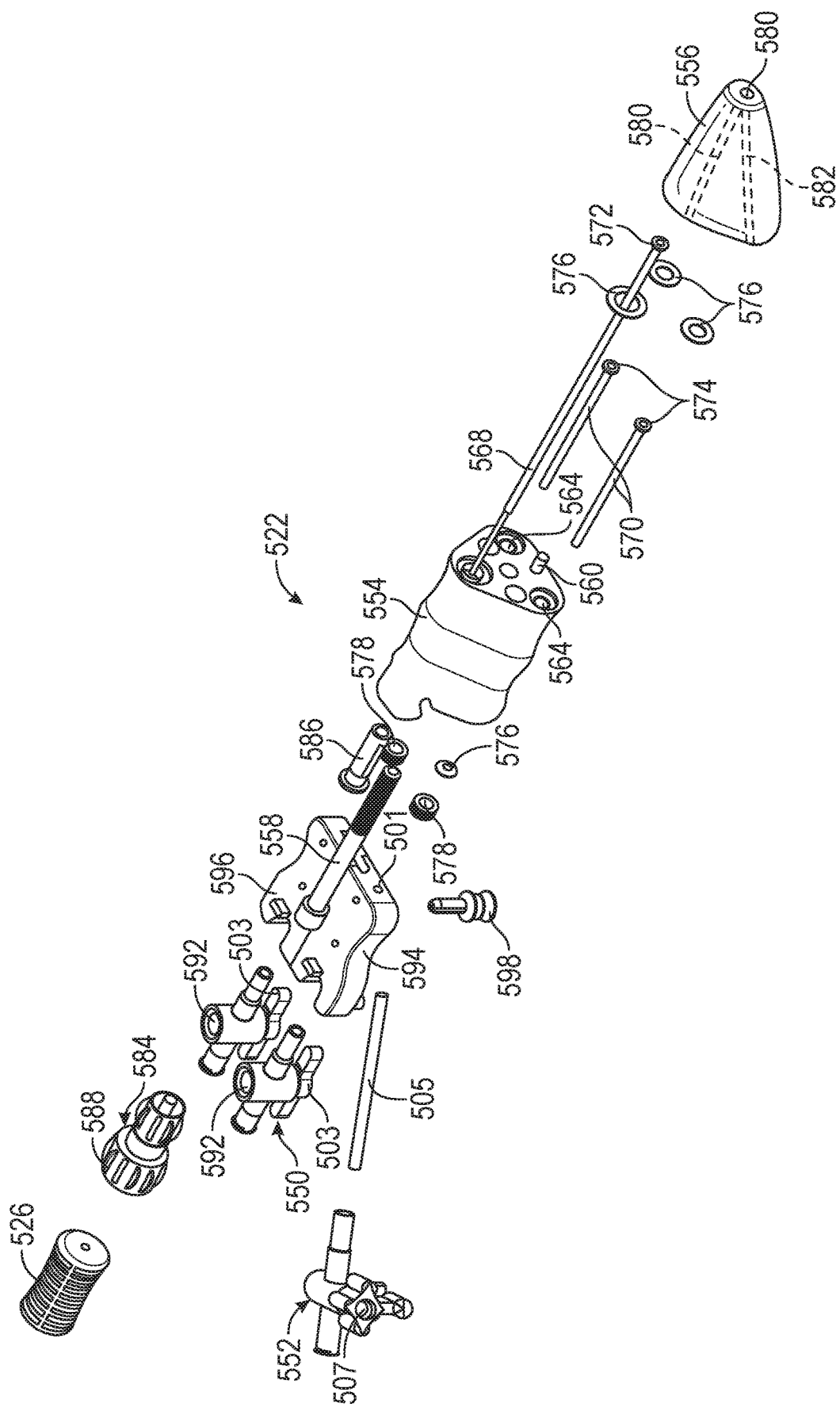
FIG. 19 is an exploded view of the proximal end portion of the delivery apparatus of FIG. 11.

As shown in FIGS. 17-19, the handle 522 of the third catheter 508 can include a housing 546, an actuation lock mechanism 548, a clasp control mechanism 550, and a flushing mechanism 552. Referring to FIG. 17, a distal end portion of the housing 546 can be coupled to the proximal end portion 520a of the outer shaft 520. The actuation lock mechanism 548, the clasp control mechanism 550, and a flushing mechanism 552 can be coupled to a proximal end of the housing 546. The actuation lock mechanism 548 can be configured to selectively lock the position of the actuation shaft 512 relative to the housing 546 and the outer shaft 520. The clasp control mechanism 550 can also be coupled to proximal end portions of the clasp control members 524 and can be configured to secure the clasp control members 524 relative to the handle 522 and to move the clasp control members 524 relative to the outer shaft 520 and the actuation shaft 512. The flushing mechanism 552 can be configured for flushing (e.g., with a saline solution) the outer shaft 520 prior to inserting the outer shaft 520 into a patient's vasculature.

As best shown in FIGS. 18-19, the housing 546 of the handle 522 can comprise a main body 554 and a nose portion 556 coupled to a distal end portion of the main body 554. The main body 554 and the nose portion 556 can be coupled together in various manners, including fasteners 558 and/or pins 560 (e.g., as shown in the illustrated embodiment), adhesive, and/or other coupling means. The housing 546 can be formed from various materials, including polymers (e.g., polycarbonate).

The main body 554 of the housing 546 can comprise a plurality of lumens, including an actuation shaft lumen 562, control member lumens 564 (FIG. 19), and a flushing lumen 566 that is fluidly connected to the actuation shaft lumen 562 (FIG. 18). As best shown in FIG. 19, the main body 554 can also include a plurality of tubes (e.g., hypotubes), including an actuation tube 568 and control member tubes 570 that are disposed at least partially in the actuation shaft lumen 562 and the control member lumens 564, respectively. The tubes 568, 570 can be axially movable (e.g., slidable) relative the lumens 562, 564, respectively.

The proximal end of the actuation tube 568 can extend proximally from the main body 554 and can be coupled to the knob 526 and to the proximal end portion 512a of the actuation shaft 512. The proximal ends of the control member tubes 570 can extend proximally from the main body 554 and can be coupled to the clasp control mechanism 550 and the clasp control members 524.

The distal ends of the tubes 568, 570 can comprise flanges 572, 574 configured to engage a stopper to limit the axial movement of the tubes 568, 570 relative to the housing 546. For example, the flanges 572, 574 can be configured to contact respective surfaces of the main body 554 (e.g., a lip) to prevent to tubes 568, 570 from withdrawing completely from the proximal ends of the lumens 562, 564, respectively.

The actuation tube 568 can be configured to receive and be coupled to the proximal end portion of the actuation shaft 512. The control member tubes 570 can be configured to receive portions of the clasp control mechanism 550, as further described below. The tubes 568, 570 can be formed from various materials, including polymers and metals (e.g., stainless steel).

In some embodiments, the main body 554 can include a plurality of seal members 576 (e.g., O-rings) configured to prevent or reduce blood leakage through the lumens and around the shafts and/or tubes. The seal members can be secured relative to the main body 554, for example, by fasteners 578 (e.g., hollow-lock or socket-jam set screws).

As best shown in FIG. 19, the nose portion 556 of the housing 546 can comprise a plurality of lumens, including an actuation shaft lumen 580 and control member lumens 582. The actuation shaft lumen 580 of the nose portion 556 can be extend coaxially with the actuation shaft lumen 562 of the main body 554. Proximal ends of the control member lumens 582 of the nose portion 556 can be aligned with the control member lumens 564 of the main body 554 at the proximal end of the nose portion 556 (i.e., the lumens 582, 564 are in the same plane). The control member lumens 582 can extend towards each other from their proximal ends at an angle (i.e., relative to the control member lumens 564 of the main body 554), and distal ends of the control member lumens 582 can intersect the actuation shaft lumen 580 of the nose portion 556 at a location near the distal end of the nose portion 556. In other words, the proximal ends of the lumens 582 are in a first plane that is parallel to a longitudinal axis of the catheter (i.e., the plane of the control member lumens 564 of the main body 554), and the distal ends of the lumens 582 are in a second plane that is parallel to a longitudinal axis of the catheter (i.e., the plane of the actuation shaft lumen 562 of the main body 554).

As best shown in FIG. 18, the actuation shaft lumen 580 of the nose portion 556 can be configured to receive the proximal end portion of the outer shaft 520. The proximal end portion of the outer shaft 520 can be coupled to the nose portion 556 in various ways such as with adhesive, fasteners, frictional fit, and/or other coupling means.

Referring still to FIG. 18, the actuation lock mechanism 548 of the handle 522 can be coupled to the proximal end portion of the main body 554 of the housing 546 and to the actuation tube 568. The actuation lock mechanism 548 can be configured to selectively control relative movement between the actuation tube 568 and the housing 546. This, in turn, selectively controls relative movement between the actuation shaft 512 (which is coupled to the actuation tube 568) and the outer shaft 520 (which is coupled to the nose portion 556 of the housing 546).

In some embodiments, the actuation lock mechanism 548 can comprise a lock configuration, which prevents relative movement between the actuation tube 568 and the housing 546, and a release configuration, which allows relative movement between the actuation tube 568 and the housing 546. In some embodiments, the actuation lock mechanism 548 can be configured to include one or more intermediate configurations (i.e., in addition to the lock and release configuration) which allow relative movement between the actuation tube 568 and the housing 546, but the force required to cause the relative movement is greater than when the actuation lock mechanism is in the release configuration.

As shown in FIG. 18 of the illustrated embodiment, the actuation lock mechanism 548 can comprise a lock (e.g., a Tuohy-Borst adapter) 584 and a coupler (e.g., a female luer coupler) 586. The coupler 586 can be attached to the distal end of the lock 584 and coupled to the proximal end of the main body 554 of the housing 546. The actuation tube 568 can extend coaxially through the lock 584 and the coupler 586. As such, rotating a knob 588 of the lock 584 in a first direction (e.g., clockwise) can increase the frictional engagement of the lock 584 on the actuation tube 568, thus making relative movement between the actuation tube 568 and the housing 546 more difficult or preventing it altogether. Rotating a knob 588 of the lock 584 in a second direction (e.g., counterclockwise) can decrease the frictional engagement of the lock 584 on the actuation tube 568, thus making relative movement between the actuation tube 568 and the housing 546 easier.

In other embodiments, actuation lock mechanism 548 can comprise other configurations configured for preventing relative movement between the actuation tube 568 and the housing 546. For example, the actuation lock mechanism 548 can include a lock configured similar to a stopcock valve in which a plunger portion of valve selectively engages the actuation tube 568.

In some embodiments, the actuation lock mechanism 548 can include a release member (e.g., a set screw or a pin). The release member can extend into the housing 546 and can selectively engage the actuation tube 568. When the release member is engaged with the actuation tube 568 (e.g., by inserting the release member into the housing 546 and into contact with the actuation tube 568), the release member can, for example, prevent the actuation tube 568 and thus the actuation shaft 512 from being completely withdrawn from their respective lumens 568, 580 (e.g., when actuating the anchors 204). When the release member is released from the actuation tube 568 (e.g., by withdrawing it from the housing 546 and/or moving it out of contact with the actuation tube 546), the actuation tube 568 and thus the actuation shaft 512 can be completely withdrawn from their respective lumens 568, 580 (e.g., when releasing the prosthetic spacer device 200 from the delivery apparatus 502).

The clasp control mechanism 550 can comprise an actuator member 590 and one or more locking members 592 (e.g., two in the illustrated embodiment). A distal end portion of the actuator member 590 can be coupled to the control member tubes 570, which extend from the proximal end of the main body 554 of the housing 546, as best shown in FIG. 18. The locking members 592 can be coupled to a proximal end portion of the actuator member 590.

As shown in the illustrated embodiment, the actuator member 590 can, optionally, comprise a first side portion 594 and a second side portion 596 selectively coupled to the first side portion 594 by a connecting pin 598. The actuator member 590 can be configured such that the first and second side portions 594, 596 move together when the connecting pin 598 is inserted through the first and second side portions 594, 596. When the connecting pin 598 is withdrawn, the first and second side portions 594, 596 can be moved relative to each other. This can allow the clasp control members 524 (which are releasably coupled to the first and second side portions 594, 596 by the locking members 592) to be individually actuated.

The connection between the first and second side portions 594, 596 can be configured such that the first and second side portions 594, 596 can move axially (i.e., proximally and distally) but not rotationally relative to each other when the connecting pin 598 is withdrawn. This can be accomplished, for example, by configuring the first side portion 594 with keyed slot or groove and configuring the second side portion 596 with a keyed projection or tongue that corresponds to the keyed slot or groove of the first side portion 594. This can, for example, prevent or reduce the likelihood that the clasp control members 524 from twisting relative to the outer shaft 520.

The first and second side portions 594, 596 can include axially extending lumens 501. Distal ends of the lumens 501 can be configured to receive the proximal end portions of the control member tubes 570. Proximal ends of the lumens 501 can be configured to receive portions of the locking members 592. As noted above, the proximal end portions of the clasp control members 524 extend through respective locking members 592.

The locking members 592 can be configured to selectively control relative movement between a clasp control member 524 and the respective first or second side portion 594, 596 of the actuator member 590. The locking members 592 can comprise a lock configuration, which prevents relative movement between a clasp control member 524 and the respective first or second side portion 594, 596, and a release configuration, which allows relative movement between a clasp control member 524 and the respective first or second side portion 594, 596. In some embodiments, the locking members 592 can also comprise one or more intermediate configurations (i.e., in addition to the lock and release configuration) which allows relative movement between a clasp control member 524 and the respective first or second side portion 594, 596, but the force required to cause the relative movement is greater than when the locking members 592 are in the release configuration.

As shown in the illustrated embodiment, the locking members 592 can be configured similar to stopcock valves. Thus, rotating knobs 503 in a first direction (e.g., clockwise) can increase the frictional engagement between the locking members 592 on the clasp control members 524 and make relative movement between a clasp control member 524 and the respective first or second side portion 594, 596 more difficult or prevent it altogether. Rotating knobs 503 in a second direction (e.g., counterclockwise) can decrease the frictional engagement between the locking members 592 on the clasp control members 524 and make relative movement between a clasp control member 524 and the respective first or second side portion 594, 596 easier. In other embodiments, the locking members 592 can comprise other configurations configured for preventing relative movement between the locking members 592 on the clasp control members 524.

The flushing mechanism 552 can comprise a flushing tube 505 and a valve 507 (e.g., a stopcock valve). A distal end of the flushing tube 505 can be coupled to and in fluidic communication with the flushing lumen 566 and thus with the actuation shaft lumen 562 of the main body 554. A proximal end of the flushing tube 505 can be coupled to the valve 507. In this manner, the flushing mechanism 552 can be configured for flushing (e.g., with a saline solution) the outer shaft 520 prior to inserting the outer shaft 520 into a patient's vasculature.

The clasp control members 524 can be configured to manipulate the configuration of the clasps 206, as further described below. As best shown in FIG. 15, each of the clasp control members 524 can be configured as a suture (e.g., wire or thread) loop. Proximal end portions of the clasp control members 524 can extend proximally from the proximal end portion of the clasp control mechanism 550 and can be releasably coupled to the locking members 592 of the clasp control mechanism 550.

From the locking members 592, the clasp control members 524 can form loops extending distally through the lumens 501 of the clasp control mechanism 550, through the control member tubes 570, the control member lumens 564, 582 of the handle 522, and through the control member lumens 540 of the outer shaft 520. The clasp control members 524 can extend radially outwardly from the lumens 540, for example, through the ports 533 (FIG. 13) of the coupler 514. The clasp control members 524 can then extend through openings 234 of the clasps 206 (e.g., similar to the openings 142 of the prosthetic spacer device 100). The clasp control members 524 can then extend proximally back to the coupler 514, radially inwardly through the ports 533 of the coupler 514, and then proximally through the outer shaft 520 and the handle 522, and to the locking members 592 of the clasp control mechanism 550.

In FIG. 15, the clasp control members 524 are shown slacken and the clasps 206 are partially open in order to illustrate the clasp control members 524 extending through the openings 234 of the clasps 206. However, ordinarily when the clasp control members 524 are slacken, the clasps 206 would be in the closed configuration.

As shown in the illustrated embodiment, each of the clasp control members 524 can extend through multiple control member lumens 540 of the outer shaft 520. For example, each of the clasp control members 524 can be looped through two of the lumens 540. In other embodiments, each of the clasp control members 524 can be disposed in a single control member lumen 540. In yet other embodiments, multiple clasp control members 524 can be disposed in a single control member lumen 540.

With the clasp control members 524 coupled to the clasps 206, the clasp control mechanism 550 can be used to actuate the clasps 206 between open and closed configurations. The clasps 206 can be opened by moving the actuator member 590 proximally relative to the knob 526 and the housing 546. This increases tension of the clasp control members 524 and causes the clasp 206 to move from the closed configuration to the open configuration. The clasps 206 can be closed by moving the actuator member 590 distally relative to the knob 526 and the housing 546. This decreases tension on the clasp control members 524 and allows the clasp 206 to move from the open configuration to the closed configuration. The clasps 206 can be individually actuated by removing the connecting pin 598 and moving the first or second side portions 594, 596 relative to each other, the knob 526, and the housing 546.

When the handle 522 is assembled as best shown in FIG. 17-18, the actuation shaft 512 can extend distally from the knob 526, through the actuation tube 568, through the actuation lumens 562, 580 of the housing 546, through the actuation shaft lumen 538 of the outer shaft 520, and through the coupler 514.

Figure 20:
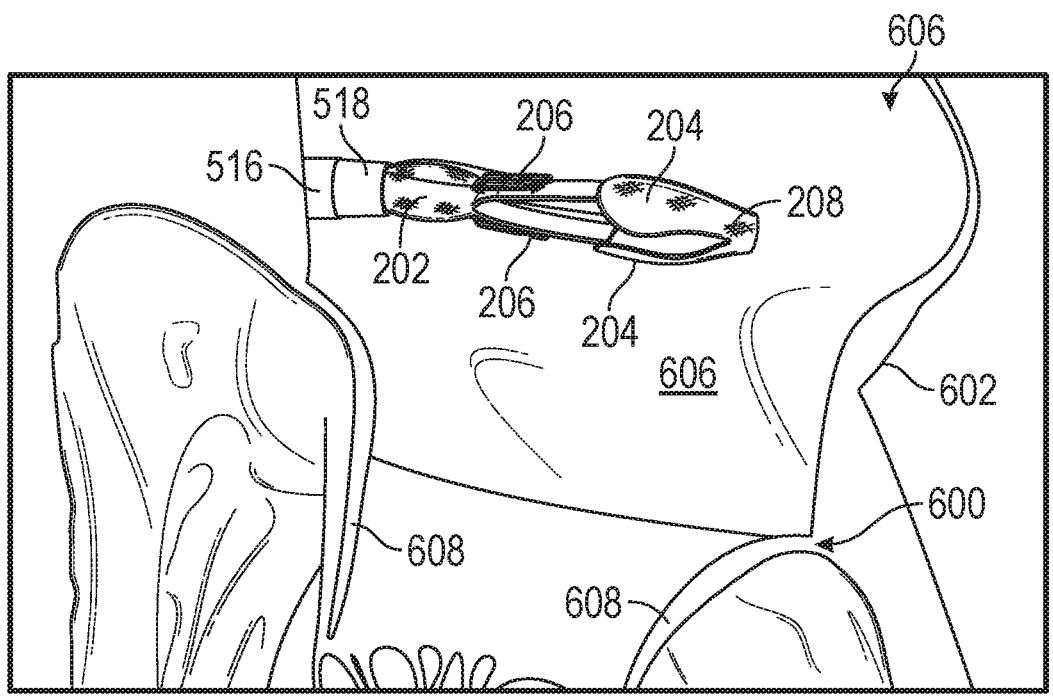
FIGS. 20-24 illustrate an exemplary implantation procedure of the prosthetic spacer device of FIG. 6 using the delivery assembly of FIG. 11 to repair a native mitral valve of a heart, which is partially shown.
Figure 21:
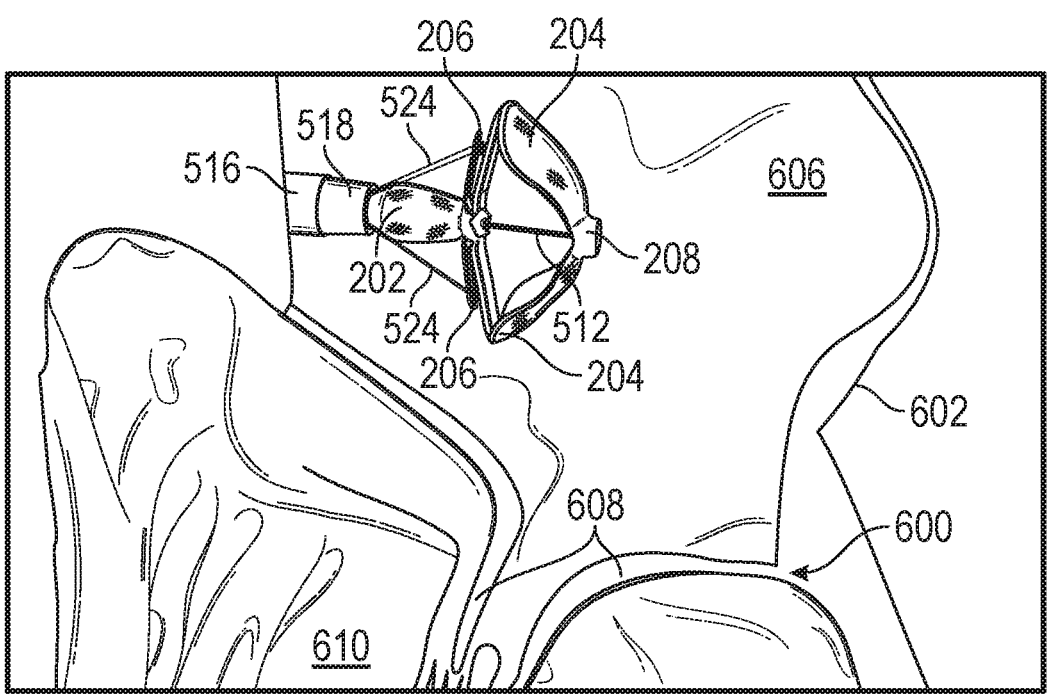

FIGS. 20-27 show the delivery assembly 500 being used, for example, to implant the prosthetic spacer device 200 in native mitral valve 600 of a heart 602 using a transseptal delivery approach. Although not shown, a guide wire can be inserted into the patient's vasculature (e.g., a femoral vein) through an introducer sheath. The guide wire can be advanced through the femoral vein, through the inferior vena cava, into the right atrium, through the interatrial septum (e.g., via the fossa ovalis), and into the left atrium 606. The first sheath 516 of the first catheter 504 can be advanced over the guide wire such that a distal end portion of the first sheath 516 is disposed in the left atrium 606, as best shown in FIG. 20.

With the prosthetic spacer device 200 coupled to the third catheter 508 (e.g., as shown in FIGS. 12A and 12B) and configured in a radially compressed, delivery configuration, the prosthetic spacer device 200 can be loaded into the second sheath 518 of the second catheter 506, which retains the prosthetic spacer device 200 in the delivery configuration. In this manner, the distal end portion of the second sheath 518 serves as a delivery capsule for the prosthetic implant 200. In some embodiments, the radially compressed, delivery configuration can be an axially elongate configuration (e.g., similar to the configuration shown in FIG. 20). In other embodiments, the radially compressed, delivery configuration can be an axially foreshorten configuration (e.g., similar to the configuration shown in FIG. 22). The second catheter 506 along with the prosthetic spacer device 200 and the third catheter 508 can then be advanced together through the first catheter 504 until a distal end portion of the sheath 518 extends outwardly from the distal end portion of the first sheath 516 and is disposed in the left atrium 606, as shown in FIG. 20.

As shown in FIG. 20, the prosthetic spacer device 200 can be exposed from the second sheath 518 by distally advancing the outer shaft 520 and the actuation shaft 512 of the third catheter 508 relative to the second sheath 518 and/or retracting the second sheath 518 relative to the outer shaft 520 and the actuation shaft 512, thus forcing the anchors 204 out of the second sheath 518. Once exposed from the second sheath 518, the anchors 204 can be folded by retracting the actuation shaft 512 of the third catheter 508 relative to the outer shaft 520 of the third catheter 508 and/or by advancing the outer shaft 520 relative to the actuation shaft 512, causing the anchors 204 to bend from the radially compressed configuration shown in FIG. 20, to the partially folded configuration shown in FIG. 21, and then to the fully folded configuration shown in FIG. 22. This can be accomplished, for example, by placing the actuation lock mechanism 548 in the release configuration (e.g., by rotating the knob 588 counterclockwise relative to the handle 522) and then moving the knob 526 proximally relative to the housing 546. At any point in the procedure, the physician can lock the relative position of the actuation shaft 512 and the outer shaft 520, and thus the position of the anchors 204, by actuating the actuation locking mechanism 548.

Figure 22:
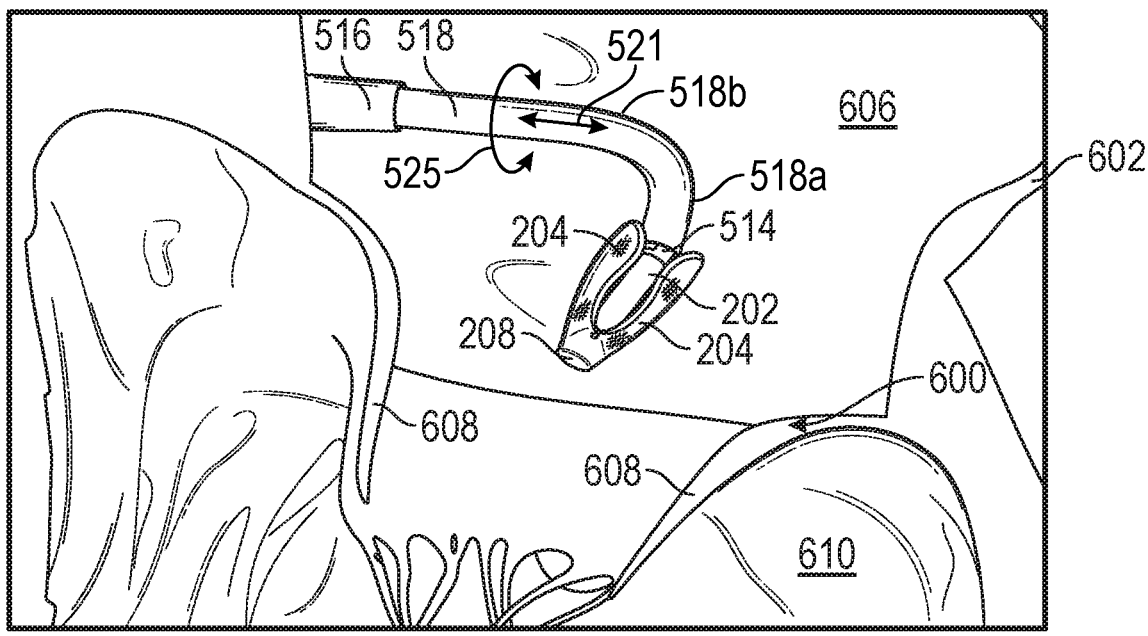

The prosthetic spacer device 200 can then be positioned coaxial relative to the native mitral valve 600 by manipulating (e.g., steering and/or bending) the second sheath 518 of the second catheter 506, as shown in FIG. 22. The prosthetic spacer device 200 can also be rotated (e.g., by rotating the housing 546) relative to the native mitral valve 600 such that the anchors 204 align with native leaflets 608 of the mitral valve 600. The curvature of the second sheath 518 can be adjusted (e.g., with the steering mechanism) so that a distal steerable section 518a extends at about a 90-degree angle relative to a section 518b that extends proximally from the steerable section 518a. Advantageously, this positions the steerable distal section 518a and the prosthetic spacer device 200 along an axis that is substantially perpendicular to a plane defined by the native mitral valve. Stated another way, the axis extending through the steerable distal section 518a and the prosthetic spacer device 200 is coaxial or substantially parallel to the flow path of the native mitral valve.

Retracting or advancing the second sheath 518 of the second catheter 506 and the outer shaft 520 of the third catheter 508 (e.g., in the directions shown by the arrow 521 in FIG. 22) relative to the first sheath 516 of the first catheter 504 and the left atrium 606 moves the outer shaft 520 of the third catheter 508 and the prosthetic spacer device 200 in the medial and lateral directions (e.g., in the directions shown by arrow 523 in FIG. 27A) relative to the native leaflets 608. As the second sheath 518 and outer shaft 520 are advanced and/or retracted, the positioning of the prosthetic spacer device 200 relative to the native mitral valve in the superior/inferior directions (e.g., up/down in the orientation shown in FIG. 22) remains at least substantially constant, and/or the second sheath 518 does not "whip" due to the configuration of the steering mechanism of the second catheter 506, which is described above. Rotating (which can also be referred to as "torquing") the second sheath 518 of the second catheter 506 (e.g., in the directions shown by the arrow 525 in FIG. 22) relative to the first sheath 516 of the first catheter 504 and the left atrium 606 pivots the outer shaft 520 of the third catheter 508 and the prosthetic spacer device 200 in the anterior/posterior directions (e.g., in the directions shown by arrow 527 in FIG. 27A). The prosthetic spacer device 200 can also be rotated (e.g., by rotating the housing 546) relative to the native mitral valve 600 in order to align the anchors 204 with native leaflets 608 of the native mitral valve 600. The positioning of the prosthetic spacer device 200 relative to the native mitral valve in the superior/inferior directions (e.g., up/down in the orientation shown in FIG. 22) can be adjusted by retracting/advancing the outer shaft 520 of the third catheter 508 relative to the second sheath of the second catheter 506. Thus, one advantage of the disclosed delivery apparatus is that the positioning of the prosthetic spacer device can be adjusted independently in three directions (i.e., the medial/lateral, anterior/posterior, and superior/inferior directions). For example, actuating the delivery apparatus such that the prosthetic spacer device moves in the medial/lateral directions does not affect the positioning of the prosthetic spacer device in the anterior/posterior directions or the superior/inferior directions. The three-way and/or independent maneuverability of the delivery apparatus 502 therefore allows the practitioner to accurately and/or precisely position the prosthetic spacer device 200 at the desired implantation location relative to the native leaflets (e.g., at the A2/P2 positions near the center of the coaptation line of the native leaflets) in a relatively quick and/or easy manner.

Figure 23:
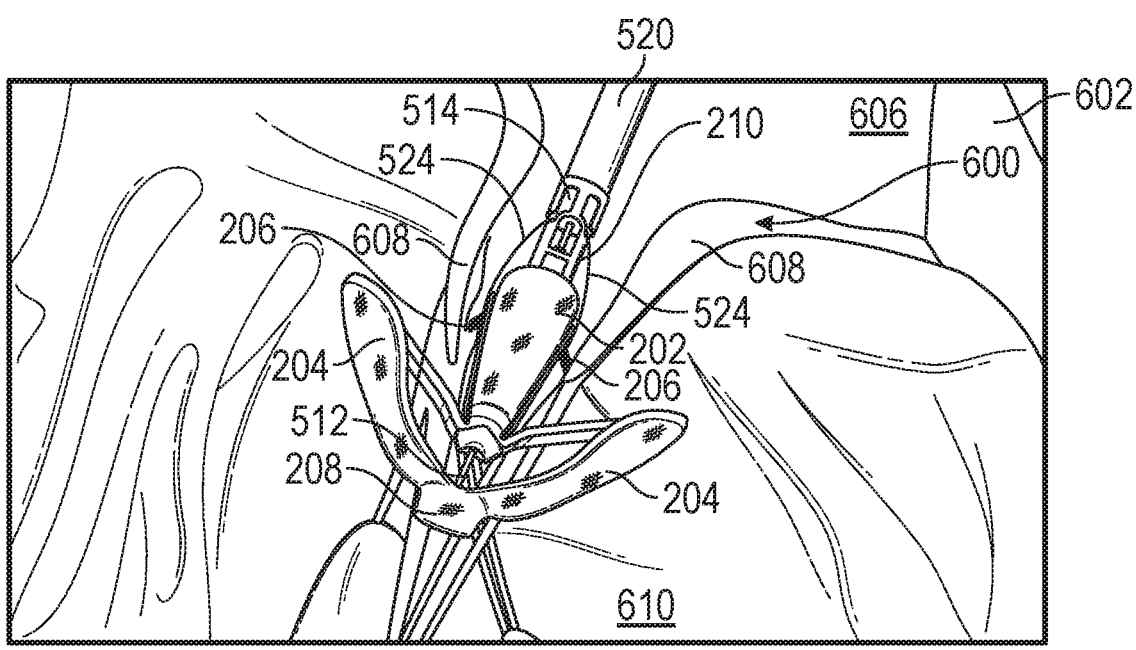

The anchors 204 of the prosthetic spacer device 200 can then be partially opened (i.e., moved radially outwardly relative to the spacer member 202) to the configuration shown in FIG. 23 by moving the knob 526 distally relative to the housing 546. The prosthetic spacer device 200 can then be advanced through the annulus of the native mitral valve 600 and at least partially into the left ventricle 610. The prosthetic spacer device 200 is then partially retracted such that the anchors 204 are positioned behind the ventricular portions of the leaflets 608 (e.g., at the A2/P2 positions) and the spacer member 202 is disposed on the atrial side of the leaflets 608. Alternatively, the prosthetic spacer device 200 can be advanced through the native valve in the fully folded configuration (as shown in FIG. 22), after which the anchors 204 can be opened.

Figure 24:
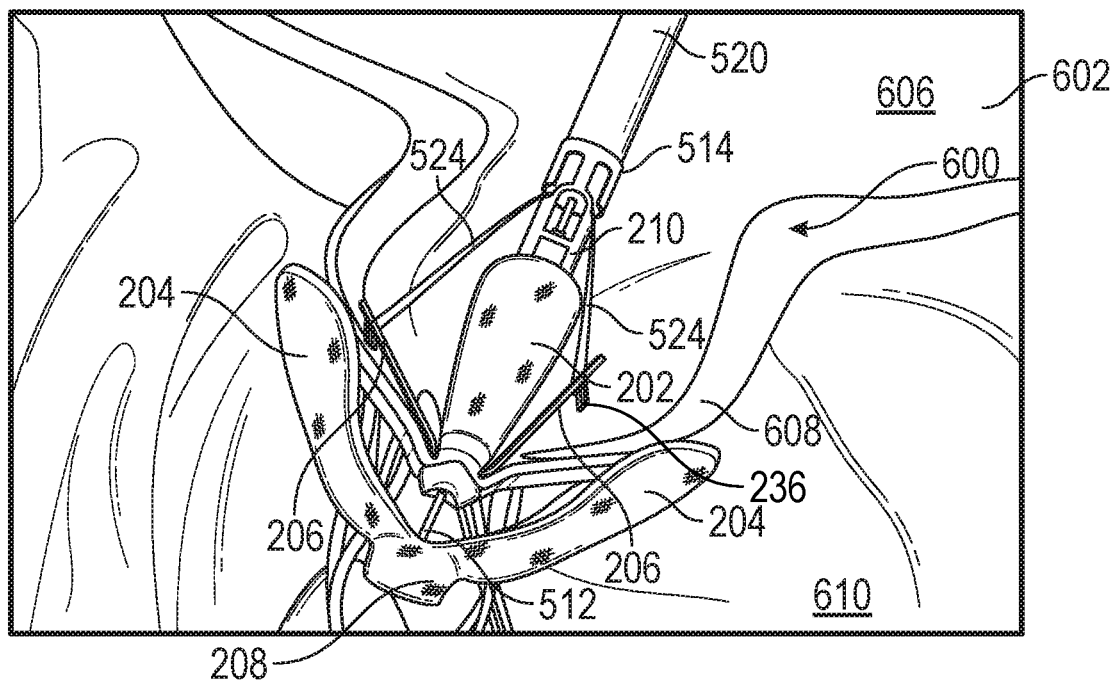

In this configuration, the native leaflets 608 can be secured relative to the anchors 204 by capturing the native leaflets with the clasps 206. The native leaflets 608 can be captured simultaneously or separately by actuating the actuator member 590. For example, FIG. 24 shows separate leaflet capture. This can be accomplished by removing the pin 598 from the actuator member 590 and moving the first or second side portions 594, 596 relative to each other, the knob 526, and the housing 546. Moving the first or second side portions 594, 596 distally relative to the knob 526 and the housing 546 closes the clasps 206 on the native leaflets 608 (e.g., as shown by the left clasp 206 as illustrated in FIG. 24). Moving the first or second side portions 594, 596 proximally relative to the knob 526 and the housing 546 opens the clasps 206 (e.g., as shown by the right clasp 206 as illustrated in FIG. 24). Once a clasp 206 is closed, a physician can re-open the clasp 206 to adjust the positioning of the clasp 206.

As the clasps 206 re-open, the clasps 206 initially move radially inwardly toward the spacer member 202 (e.g., as shown with the right clasp 206 in FIG. 24) until the clasps 206 contact the spacer member 202 (e.g., as shown in FIG. 23). In some instances, barbs 236 of the clasps 206 may retain and pull the native leaflets 608 toward the spacer member 202 as the clasps 206 are re-opened. Once the clasps 206 contact the spacer member 202, further tensioning the clasp control member 524 moves the clasps 206 slightly proximally relative to the spacer member 202 (and causes the anchors 204 to slightly unfold). The proximal movement of the clasps 206 can, for example, withdraw the barbs 236 from the native leaflets 608, which can facilitate repositioning and/or retrieval of the prosthetic spacer device 200.

Figure 25:
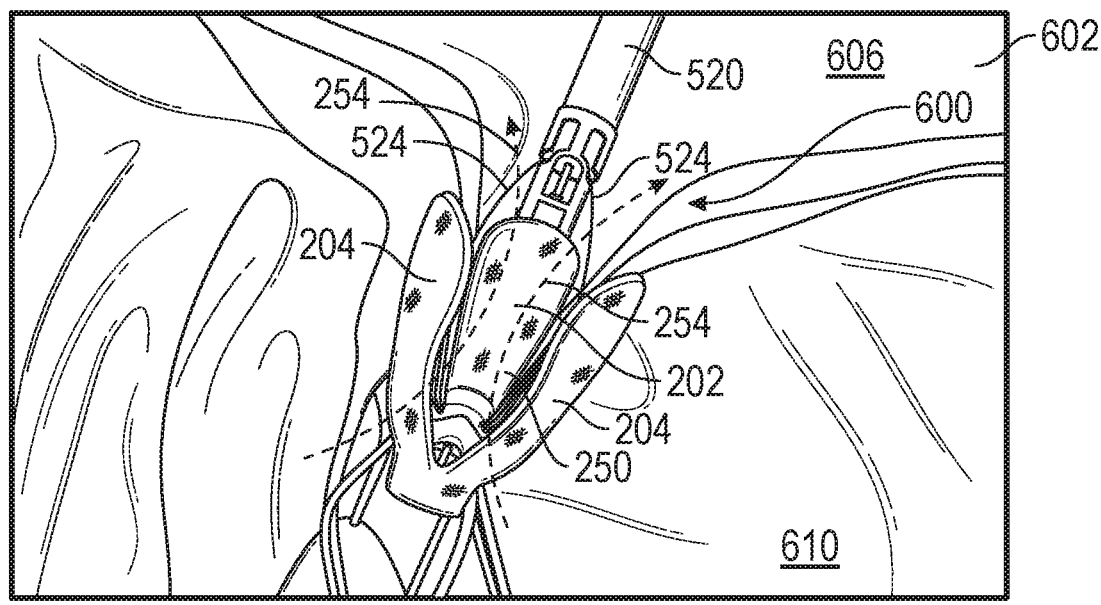
FIG. 25 illustrates the prosthetic spacer device of FIG. 6 situated between the leaflets of the mitral valve prior to being released from the delivery assembly and allowing regurgitant blood flow through the device.

With both of the native leaflets 608 secured within the clasps 206, the physician can move the knob 526 proximally relative to the housing 546. This pulls the anchors 204 and, thus, the native leaflets 608, radially inwardly against the spacer member 202, as shown in FIG. 25. The physician can then observe the positioning and/or the amount of regurgitation through the spacer device into the left atrium.

For example, FIG. 25 illustrates the prosthetic spacer device 200 in the deployed configuration in the mitral valve 600 prior to release of the device from the delivery apparatus. As the left ventricle 610 contracts, blood can flow regurgitatively from the left ventricle 610 to the left atrium 606 through the spacer member 202 along the flow path 254. In some embodiments, the leaflets 608 can form a seal against the spacer member 202 such that a primary acute regurgitant flow is through the spacer member 202. If repositioning or removal is desired, the physician can re-open the anchors 204 and/or the clasps 206.

Figure 26:
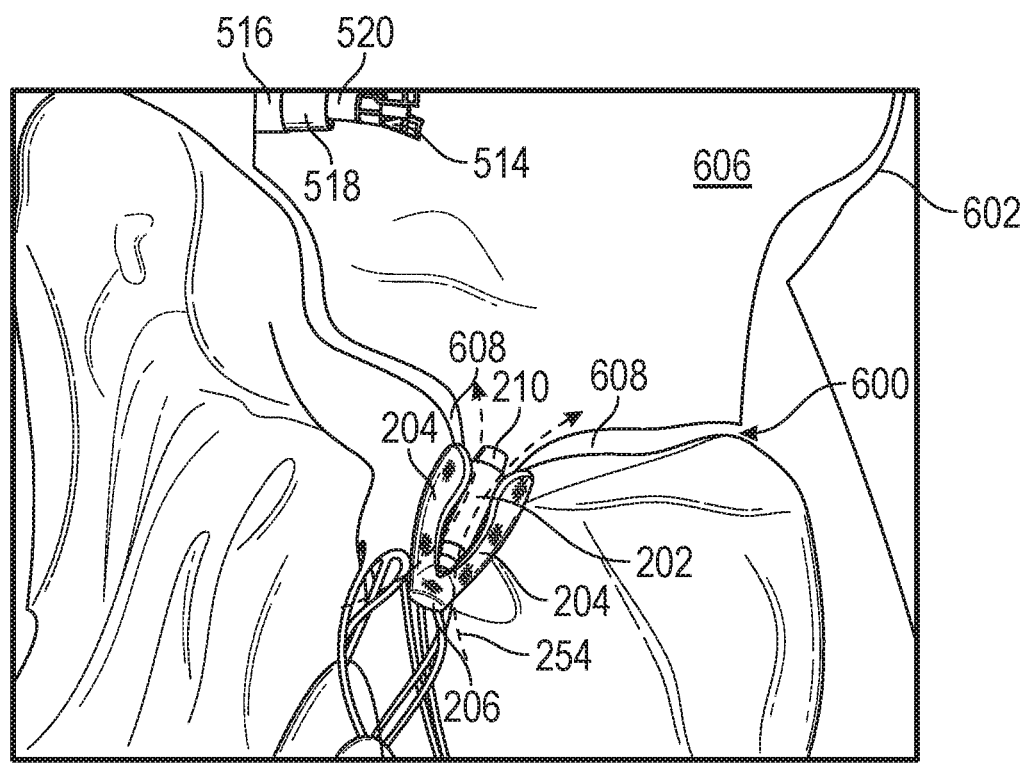
FIG. 26 illustrates the prosthetic spacer device of FIG. 25 after being released from the delivery assembly, and allowing regurgitant blood to flow through the device.

Once the desired positioning and/or acute regurgitant flow is achieved, the physician can release the prosthetic spacer device 200 from the delivery apparatus 502. The clasps 206 can be released from the delivery apparatus 502 by releasing the clasp control members 524 from the locking members 592 and unthreading the clasp control members 524 from the openings 234 of the clasps 206. The distal collar 208 of the prosthetic spacer device 200 can be released from the delivery apparatus 502 by rotating the knob 526 in the second direction relative to the housing 546 such that the actuation shaft 512 withdraws from the bore 226. The actuation shaft 512 can then be retracted proximally through the prosthetic spacer device 200 by pulling the knob 526 proximally relative to the housing 524. The proximal collar 210 of the prosthetic spacer device 200 can be released from the delivery apparatus 502 by retracting the actuation shaft 512 proximally relative to the coupler 514 such that the distal end portion of the actuation shaft 512 withdraws from the eyelets 534 of the coupler 514. This allows the flexible arms 528 of the coupler 514 to move radially outwardly away from the projections 230 of the proximal collar 210. The stabilizer members 530 of the coupler 514 can then be withdrawn from the guide openings 232 of the proximal collar 210 by pulling the housing 546 proximally, thereby releasing the prosthetic spacer device 200 from the delivery apparatus 502 as shown in FIG. 26.

The shafts 512, 520 of the third catheter 308 can then be retracted proximally into the second sheath 518 of the second catheter 306, and the second sheath 518 of the second catheter 506 can be retracted proximally into the first sheath 516 of the first catheter 504. The catheters 504, 506, 508 can then be retracted proximally and removed from the patient's vasculature.

Figure 27A:
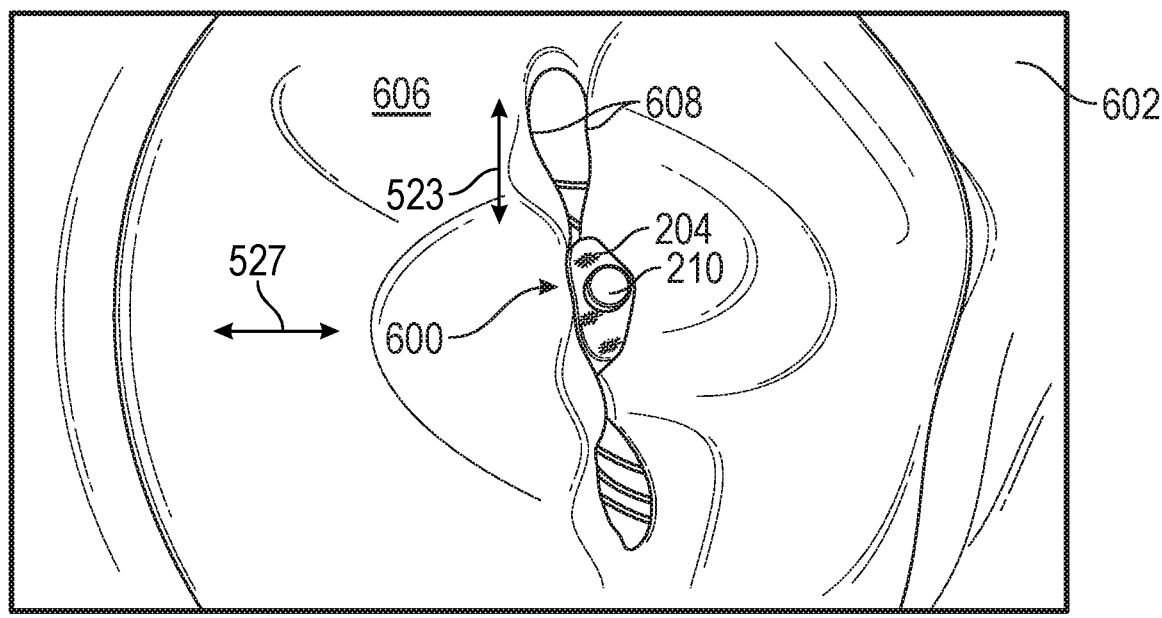
FIG. 27A is a perspective view illustrating the mitral valve and the floor of the left atrium with the prosthetic spacer device deployed between the native leaflets and causing the leaflets to form a double orifice during ventricular diastole.

With the prosthetic spacer device 200 implanted at the A2/P2 position, the native mitral valve 600 can, in some embodiments, comprise a double orifice during ventricular diastole, as shown in FIG. 27A. During ventricular systole, the native leaflets 608 can coapt together and/or against the prosthetic spacer device 200 (e.g., to prevent or reduce mitral regurgitation through the leaflets). However, the prosthetic spacer device 200 can provide for acute regurgitant or retrograde blood flow through the spacer member 202 at the time the device is implanted. As used herein, the phrases "at the time of implantation," "at the time of deployment," etc., refer to the time at which the native leaflets are captured between the anchor members and the spacer member such that the prosthetic spacer device is ready to be released from the delivery apparatus, and the minutes or hours (e.g., up to 12 hours) following the release of the prosthetic spacer device from the delivery apparatus.

For example, in certain configurations the volume of regurgitant blood flow through the spacer member 202 at the time that the prosthetic spacer device is deployed can be equivalent to mitral regurgitation having an angiographic grade of at least MR>2+, at least MR>3+, or at least MR>4+. In other examples, the volume of regurgitant blood flow through the spacer member 202 at the time that the prosthetic spacer device is deployed can be the same, or nearly the same, as the volume of regurgitant blood flow through the native mitral valve before the device was implanted.

For example, a patient with moderate-to-severe mitral regurgitation (e.g., having an angiographic grade of MR>3+) may have regurgitant blood flow equivalent to 30%, 40%, or more than 40% of their left ventricle stroke volume during each cardiac cycle before implantation of the prosthetic spacer device. As used herein, the term "left ventricle stroke volume" refers to the difference between the end-diastolic volume of the left ventricle and the end-systolic volume of the left ventricle. In adult humans, the end-diastolic volume of the left ventricle may be from 120 mL to 165 mL, 130 mL to 155 mL, or 140 mL to 150 mL. In certain examples, the mean end-diastolic volume of the left ventricle in male and female subjects ranging in age from 20 to 79 years old can be 142 mL±21 mL. In humans, the end-systolic volume of the left ventricle may be from 30 mL to 60 mL, 35 mL to 55 mL, or 40 mL to 50 mL. In certain examples, the mean end-systolic volume of the left ventricle in male and female subjects ranging in age from 20 to 79 years old can be 47 mL±10 mL. In an adult human heart, the left ventricle stroke volume may be from 60 mL to 135 mL, 70 mL to 120 mL, 80 mL to 110 mL, 81 mL to 109 mL, or 90 mL to 100 mL. In certain examples, the mean left ventricle stroke volume of a human heart in male and female subjects ranging in age from 20 to 79 years old can be 95 mL±14 mL. In certain examples, MR>3+ can be associated with a regurgitant blood flow volume from the left ventricle into the left atrium of greater than 30 mL, greater than 40 mL, greater than 50 mL, 30 mL to 80 mL, 40 mL to 70 mL, 45 mL to 65 mL, or 50 mL to 60 mL. In a trial of the Edwards Lifesciences Corporation PASCAL® device including a total of 23 participants in which five participants presented with MR graded at 3+ and 18 participants presented with MR graded at 4+, the mean regurgitant volume of all participants was 58 mL with a standard deviation of 30 mL. (Praz et al., "Compassionate use of the PASCAL transcatheter mitral valve repair system for patients with severe mitral regurgitation: a multicentre, prospective, observational, first-in-man study," *Lancet* vol. 390, pp. 773-780, 2017).

As used herein, the term "cardiac cycle" refers to the systole stage and the diastole stage that together comprise one complete heartbeat. After the prosthetic spacer device is implanted, the volume of regurgitant blood flow through the device 200 can also be moderate-to-severe (e.g., equivalent to mitral regurgitation having an angiographic grade of MR>3+) at the time the device is deployed, or shortly thereafter. For example, a volume of the regurgitant blood flow through the spacer member 202 during each cardiac cycle can be from 5% to 30% of the left ventricle stroke volume for at least one hour, at least one day, at least one week, or at least one month after implantation. In certain examples, this can greatly reduce the stress on the left ventricle associated with a sudden reduction in mitral regurgitation.

By way of further example, a patient with severe mitral regurgitation (e.g., having an angiographic grade of MR≥4+) may have a regurgitant blood flow volume of 40% or more of the left ventricle stroke volume during each cardiac cycle before implantation of the prosthetic spacer device. After the prosthetic spacer device is implanted, the regurgitant blood flow through the device can also be severe (e.g., equivalent to mitral regurgitation having an angiographic grade of MR>4+, or not less than MR>3+) at the time the device is deployed, or shortly thereafter. For example, a volume of regurgitant blood flow through the spacer member 202 during each cardiac cycle can be equivalent to 15% to 30% of the left ventricle stroke volume for at least one hour, at least one day, at least one week, or at least one month after implantation. In other examples, the regurgitant blood flow through the device can be equivalent to MR>2+. In still other examples, the regurgitant blood flow through the device can be significant enough to reduce or prevent acute impairment of left ventricular function, such as afterload mismatch.

Figure 27B:
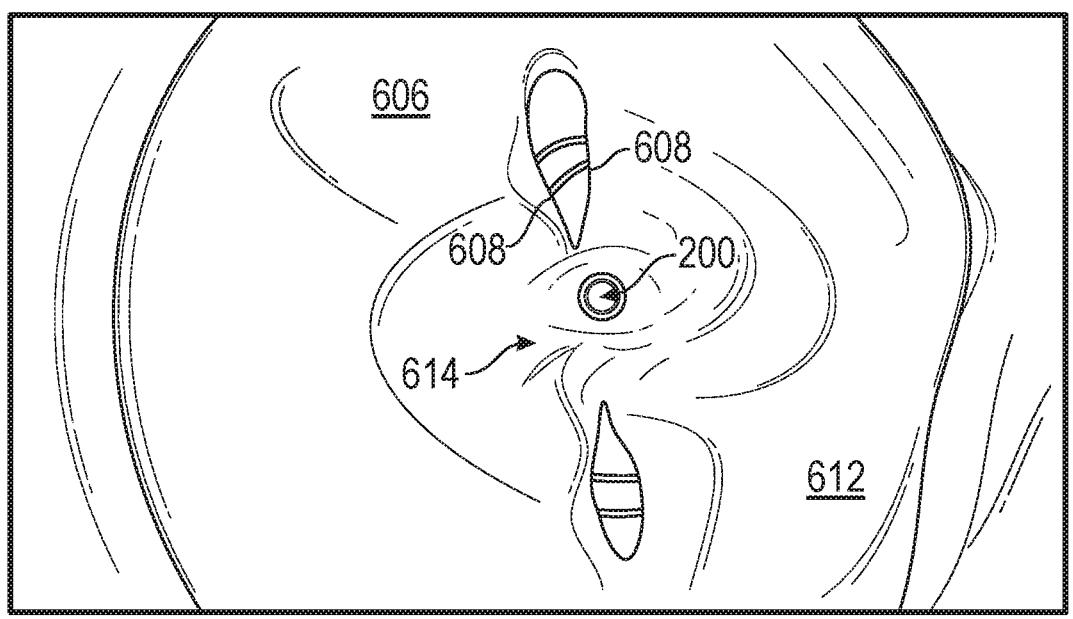
FIG. 27B is a perspective view illustrating the mitral valve and the floor of the left atrium after endothelialization of the prosthetic spacer device.

In certain examples, the covering 250 can be configured to promote tissue ingrowth into the covering, also referred to herein as "endothelialization." Endothelialization of the prosthetic spacer device 200 can slowly reduce the amount of regurgitant blood flow through the spacer member 202, and can improve the long term stability of the implant. For example, after implantation, the endothelium in contact with the various parts of the prosthetic spacer member 200 can grow into the covering 250 such that the device becomes covered or encapsulated in endothelial tissue. Encapsulation of the prosthetic spacer device 200 by the endothelium can occur over a time period of, for example, one to six months. In this manner, the endothelial tissue can use the prosthetic spacer device 200 as a scaffolding to form an endothelial "tissue bridge" extending between and coupling the mitral leaflets 608 to each other. FIG. 27B illustrates the leaflets 608 coupled together at the A2/P2 region by the prosthetic spacer device 200 after the device has been encapsulated by endothelial tissue 612 to form a tissue bridge 614.

As the device 200 endothelializes, the tissue 612 can slowly fill in and occlude the openings 252 of the covering 250. This can reduce the volume of regurgitant blood flow through the spacer member 202 during ventricular systole. In other words, as the implant 200 endothelializes, the acute regurgitant blood flow through the spacer member 202 at the time of implantation can be slowly reduced over a time period of, for example, days, weeks, or months. For example, in a patient wherein the regurgitant blood flow through the spacer member 202 is equivalent to moderate-to-severe mitral regurgitation (e.g., equivalent to an angiographic grade of MR≥3+) at the time the device 200 is deployed, the blood flow through the device can be reduced such that it is equivalent to mild-to-moderate regurgitation (e.g., equivalent to MR≤2+), equivalent to mild regurgitation (e.g., equivalent to MR≤1+), equivalent to trace regurgitation, or equivalent to no regurgitation over a period of, for example, 7 days, two weeks, one month, three months, six months, etc.

In another example, for a patient wherein the regurgitant blood flow through the spacer member 202 is equivalent to severe mitral regurgitation (e.g., equivalent to an angiographic grade of MR>4+) at the time the device 200 is deployed, the blood flow through the device can be reduced such that it is equivalent to mild-to-moderate regurgitation (e.g., MR≤2+), mild regurgitation (e.g., MR≤1+), trace regurgitation, or no regurgitation over a period of, for example, 7 days, two weeks, one month, three months, six months, etc.

In another example, in a patient wherein the regurgitant blood flow through the spacer member is from 15% to 30% of the left ventricle stroke volume at the time the device 200 is deployed, the blood flow through the spacer member can be reduced to 5% to 20% of left ventricle stroke volume, or 0% of left ventricle stroke volume (e.g., no blood flow through the device), over a period of, for example, 7 days, two weeks, one month, three months, six months, etc.

In another example, the device 200 can be configured such that regurgitant blood flow through the spacer member 202 is reduced to 0% (e.g., no blood flow through the spacer member) over a period of, for example, one day, 7 days, two weeks, one month, three months, six months, etc. In another example, the device 200 can be configured such that regurgitant blood flow through the spacer member 202 is reduced by 100%, 90%, 80%, 70%, 60%, 50%, 40%, or 30% over a period of, for example, one day, 7 days, two weeks, one month, three months, or six months, as compared to the volume of regurgitant blood flow through the device at the time of implantation.

The prosthetic spacer device embodiments herein can provide significant advantages over existing devices for treating valvular regurgitation, such as mitral regurgitation. For example, by providing a path for acute regurgitant blood flow through the spacer device that diminishes over time, the disclosed spacer devices can reduce the stress on the left ventricle associated with a sudden reduction in mitral regurgitation. This can allow the disclosed devices to be used, for example, in patients with LVEF<20%, a condition which is contraindicated for many existing treatment devices due to the risk of heart failure. Additionally, the slow reduction in regurgitant blood flow through the device as the covering endothelializes can allow the heart a longer period of time to adjust to the higher load on the left ventricle. This can reduce the risk of left ventricle overload, which can lead to heart failure or patient death.

General Considerations

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

As used herein, the term "approximately" means the listed value and any value that is within 10% of the listed value. For example, "approximately 100 degrees" means any value between 90-110 degrees, inclusive.

In view of the many possible embodiments to which the principles of the disclosed technology may be applied, it should be recognized that the illustrated embodiments are only preferred examples and should not be taken as limiting the scope of the disclosure. Rather, the scope of the disclosure is at least as broad as the following claims.

The invention claimed is:

1. A method of implanting a prosthetic device, comprising:
    advancing the prosthetic device in a compressed configuration to a native mitral valve using a delivery apparatus, the prosthetic device comprising a spacer member and a plurality of anchor members, the native mitral valve being located between a left atrium and a left ventricle of the heart;
    radially expanding the prosthetic device from the compressed configuration to an expanded configuration;
    positioning the prosthetic device such that the spacer member is located between leaflets of the native mitral valve;
    capturing the leaflets between the anchor members and the spacer member such that the prosthetic device is retained between the leaflets, and such that blood flows regurgitatively through the spacer member from the left ventricle to the left atrium;
    releasing the prosthetic device from the delivery apparatus; and
    wherein a volume of the regurgitant blood flow through the spacer member at the time the prosthetic device is released is equivalent to mitral regurgitation having an angiographic grade of MR>2+.

2. The method of claim 1, wherein prior to implanting the prosthetic device, a left ventricle ejection fraction of the left ventricle is less than 20% of an end-diastolic volume of the left ventricle.

3. The method of claim 1, wherein the volume of the regurgitant blood flow through the spacer member at the time the prosthetic device is released is equivalent to mitral regurgitation having an angiographic grade of MR>3+.

4. The method of claim 1, wherein the spacer member comprises a wire mesh.

5. The method of claim 1, wherein the spacer member comprises a porous covering.

6. A method of implanting a prosthetic device, comprising:
    advancing the prosthetic device in a compressed configuration to a native mitral valve using a delivery apparatus, the prosthetic device comprising a spacer member and a plurality of anchor members, the native mitral valve being located between a left atrium and a left ventricle of the heart;
    radially expanding the prosthetic device from the compressed configuration to an expanded configuration;
    positioning the prosthetic device such that the spacer member is located between leaflets of the native mitral valve;
    capturing the leaflets between the anchor members and the spacer member such that the prosthetic device is retained between the leaflets, and such that blood flows regurgitatively through the spacer member from the left ventricle to the left atrium;
    releasing the prosthetic device from the delivery apparatus; and
    wherein the spacer member is configured to allow a regurgitant blood flow volume through the prosthetic device from the left ventricle to the left atrium of from 5% to 30% of a left ventricle stroke volume of the left ventricle at the time the prosthetic device is released and the regurgitant blood flow volume is equivalent to mitral regurgitation having an angiographic grade of MR>2+.

7. The method of claim 6, wherein the regurgitant blood flow volume through the spacer member at the time the prosthetic device is released is equivalent to mitral regurgitation having an angiographic grade of MR>3+.

8. The method of claim 6, wherein the spacer member comprises a wire mesh.

9. The method of claim 6, wherein the spacer member comprises a porous covering.

10. A method of implanting a prosthetic device, comprising:
    advancing the prosthetic device in a compressed configuration to a native mitral valve using a delivery apparatus, the prosthetic device comprising a spacer member and a plurality of anchor members, the native mitral valve being located between a left atrium and a left ventricle of the heart;
    radially expanding the prosthetic device from the compressed configuration to an expanded configuration;
    positioning the prosthetic device such that the spacer member is located between leaflets of the native mitral valve;
    capturing the leaflets between the anchor members and the spacer member such that the prosthetic device is retained between the leaflets, and such that blood flows regurgitatively through the spacer member from the left ventricle to the left atrium;
    releasing the prosthetic device from the delivery apparatus;
    wherein the spacer member comprises a porous covering that is configured to promote tissue ingrowth such that the regurgitant blood flow through the prosthetic device from the left ventricle to the left atrium is reduced from 15% to 30% of a left ventricle stroke volume of the left ventricle and having a mitral regurgitation angiographic grade of MR>2+ at the time the prosthetic device is released, to 0% to 20% of a left ventricle stroke volume of the left ventricle over a time period of one month to six months.

11. The method of claim 10, wherein a volume of the regurgitant blood flow through the spacer member at the time the prosthetic device is released is equivalent to mitral regurgitation having an angiographic grade of MR>3+.

* * * * *